US008163776B2

(12) United States Patent
Grassetti et al.

(10) Patent No.: US 8,163,776 B2
(45) Date of Patent: Apr. 24, 2012

(54) METHOD OF IMMUNOMODULATION USING THIONE-FORMING DISULFIDES

(75) Inventors: Davide R. Grassetti, Jamestown, CA (US); Camillo Moro, Padua (IT)

(73) Assignee: Grassetti family Trust, Berkeley, CA (US)

( * ) Notice: Subject to any disclaimer, the term of this patent is extended or adjusted under 35 U.S.C. 154(b) by 861 days.

(21) Appl. No.: 10/044,463

(22) Filed: Jan. 10, 2002

(65) Prior Publication Data

US 2004/0265327 A1   Dec. 30, 2004

Related U.S. Application Data

(60) Provisional application No. 60/260,943, filed on Jan. 10, 2001.

(51) Int. Cl.
*A61K 31/44* (2006.01)
(52) U.S. Cl. .......................... 514/335; 514/333
(58) Field of Classification Search .................. 514/333, 514/335
See application file for complete search history.

(56) References Cited

U.S. PATENT DOCUMENTS

| 3,597,160 | A | | 8/1971 | Grassetti |
| 3,698,866 | A | | 10/1972 | Grassetti et al. |
| 4,152,439 | A | | 5/1979 | Grassetti |
| 4,378,364 | A | | 3/1983 | Grassetti |
| 5,662,896 | A | * | 9/1997 | Barber et al. ............... 424/93.2 |
| 5,908,861 | A | | 6/1999 | Kun |
| 6,001,555 | A | * | 12/1999 | Henderson et al. ............ 435/5 |
| 6,043,256 | A | | 3/2000 | Grassetti |

FOREIGN PATENT DOCUMENTS

| CA | 985170 | 3/1976 |
| EP | 0 194 571 A1 | 9/1986 |
| WO | WO 99/07368 | 2/1999 |

OTHER PUBLICATIONS

Toth et al. "Differential Replication of Human Immunodeficiency Virus Type 1 in CD8– and CD8+ Subsets of Natural Killer Cells" 1993, Journal of Virology, 67(10), 5879-88.*
Hardman et al., "Goodman & Gilman's the Pharmacological Basis of Therapeutics," 9th ed., 1996, pp. 51 and 57-58.*
Tagawa "Cytokine therapy for cnacer", Current Pharmaceutical design, 2000, vol. 6, 681-699.*
Oliver "T cell immune response to cancer in human and its relevance for immunodiagnosis and therapy," Cancer Surveys, 1992, vol. 13, pp. 173-204.*
Hardman et al. "Goodman& Gilman's The Pharmacological Basis of Therapeutics," $9^{th}$ ed. 1996, pp. 51 and 57-58.*
Anderson et al. (1980). "T-cell-dependent B-cell Stimulation is $H$-2 Restricted and Antigen Dependent Only at the Resting B-cell Level," *PNAS* 77(3):1612-1616.

(Continued)

*Primary Examiner* — Shengjun Wang
(74) *Attorney, Agent, or Firm* — Gary Baker; Quine Intellectual Property Law Group PC.

(57) ABSTRACT

The invention provides for the methods of modulating an immune response in an individual by administration of a thione-forming disulfide (TFD). Immunomodulatory responses include, but are not limited to, increased natural killer cell activity, expansion of NK cell population, decreased B cell population, decreased antibody production, and increased mitogenic potential. Methods of modulating such immune responses and the uses of immunomodulation are provided herein.

16 Claims, 7 Drawing Sheets

Total Splenocyte Counts

Total splenocyte count performed by trypan blue exclusion on male Balb/c mice after 6 days (n=3) or 30 days (n=8) of treatment in vivo with CPDS.
* statistically significant

OTHER PUBLICATIONS

Barnes, D and G. Sato. (1980). "Methods for Growth of Cultured Cells in Serum-Free Medium," *Anal. Biochem.* 102:255-270.

Boot, J.H. (1995). "Effects of SH-blocking Compounds on the Energy Metabolism in Isolated Rat Hepatocytes," *Cell Structure and Function* 20(3):233-238.

D'Amico, J.J and T.W. Bartram. (1960). "Thiazolethiols and Their Derivatives,"*J. Org. Chem.* 25:1336-1342.

Daves et al. (1964). "Pyrimidines. XIII. 2- and 6-Substituted 4-Pyrimidinecarboxylic Acids," *J. Heterocyclic Chem.* 1:130-133.

Dröge et al. (1991). "Modulation of Lymphocyte Functions and Immune Responses by Cysteine and Cysteine Derivatives," *Am. J. Med.* 91(3C):140-144.

Fox, H.H. and J.T. Gibas. (1958). "Nuclear Substitution Derivatives of Isonicotinic Acid," *J. Org. Chem.* 23:64-66.

Grassetti D.R. and J.F. Murray. (1967). "The Effect of 2,2'-dithiodipyridine on Thiols and Oxidizable Substrates of Ehrlich Ascites Cells and of Normal Mouse Tissues," *Biochem. Pharmacol.* 16(12):2387-2393.

Grassetti D.R. and J.F. Murray. (1968). "Restoration of Glycolysis and Respiration in Ehrlich Ascites Tumor Cells Inhibited by 2,2'-dithiodipyridine," *Biochem. Pharmacol.* 17(11):2281-2290.

Grassetti et al. (1966). "Synthesis of Some Homologs of Fluoropyruvic Acid and Their Effect of the Carbohydrate Metabolism of Ehrlich Ascites Tumor and on Lactate Dehydrogenase," J. Med. Chem. 9:149-151.

Grassetti et al. (1967). "The Effect of Some Disulfides and Thiols on the Carbohydrate Metabolism of Ehrilich Ascites Tumor," *J. Med. Chem.* 10:1170-1172.

Grassetti et al. (1970). "The Effect of Some Heterocyclic Disulfides and Thiones on the Carbohydrate Metabolism of Ehrlich Ascites Tumor," *J. Med. Chem.* 13:273-276.

Grassetti, D.R. (1970). "Effect of 6,6'-Dithiodinicotinic Acid on the Dissemination of Ehrlich Ascites Tumour," *Nature* 228(268):282-283.

Grassetti, D.R. (1984). "Metastases Limited," *Nature* 308(5959):500.

Grassetti, D.R. (1986). "6,6'-Dithiodinicotinic Acid Carboxypyridine Disulfide 6,6'Dithiobis-3-pyridinecarboxylic Acid," *Drugs of the Future* 11(7):559-561.

Grassetti, D.R. (1986). "The Antimetastatic and Tumor Growth Retarding Effects of Sulfur Containing Analogs of Nicotinamide," *Cancer Letters* 31:187-195.

Ham, R.G. and W.L. McKeehan. (1979). "Media and Growth Reqirements," *Meth. Enz.* 58:44-93.

Julius et al. (1982). "Dissociation of Two Signals Required for Activation of Resting B Cells," *PNAS* 79:1989-1993.

Mahato et al. (1997). "Cationic Lipid-Based Gene Delivery Systems: Pharmaceutical Perspectives," *Pharm. Res.* 14(7):853-859.

Möller, G. ed. (1987). "Activation Antigens and Signal Transduction in Lymphocyte Activation," Immunol Rev. 95:1-194. (Table of Contents Only).

Purnell, M.R. and W.J.D. Whish. (1980). "Novel Inhibitors of Poly(ADP-Ribose) Synthetase," *Biochem. J.* 185:775-777.

Rath, C. (1931). "Mercaptane and Sulfosäuren des Pyridins," *Justus Liebigs Ann. Chem.* 487:105119.

Sprent, J. (1978). "Restricted Helper Funtion of $F_1$ Hybrid T Cells Positively Selected to Heterologous Erythrocytes in Irradiated Parental Strain Mice II. Evidence for Restrictions Affecting Helper Cell Induction and T-B Collaboration, Both Mapping to the *K*-End of the *H*-2 Complex," *J. Exp. Med.* 147:1159-1174.

Weltin et al. (1995). "Immunosuppressive Activities of 6(5H)-Phenanthridinone, A New Poly(ADP Ribose)Polymerase Inhibitor," *Int. J. Immunopharmac.* 17(4):265-271.

Willoughby, D.A. and C. Wood. eds. (1977). "The History and Development of Levaminsole," *Forum on Immunotherapy* 1(1):3-10.

Zackheim, H.S. (1985). "Topical 6-Aminonicotinamide," Chapter 30 in *Psoriasis.* Roenick, H.H. and H.I. Maibach eds. Marcell Dekker, N.Y. pp. 361-372.

Hidore et al. (1991) "Responses of Murine Natural Killer Cells to Binding of the Fungal Target *Cryptococcus neoformans.*" *Infection and Immunity*, 59(4): 1489-1499.

Orange and Ballas (2006) "Natural Killer cells in human health and disease." *Clinical Immunology*, 118: 1-10.

Wikipedia Article "Autoimmune disease", printed Jan. 31, 2011.

Wikipedia Article "B-Cell", printed Jan. 31, 2011.

* cited by examiner

Total Splenocyte Counts

Total splenocyte count performed by trypan blue exclusion on male Balb/c mice after 6 days (n=3) or 30 days (n=8) of treatment in vivo with CPDS.
* statistically significant

NK cell activity

NK cell activity of male Balb/c mice, expressed as a percentage of specific lysis for an effector:target (E:T) ratio of 200:1, after 6 days (n=3) or 30 days (n=8) of *in vivo* treatment with CPDS.
* statistically significant

Immunophenotyping

Spleen cell subset of male Balb/c mice, after 6 days of treatment *in vivo* with CPDS, expressed as percentage of total population. Cells were labeled with fluorescent antibodies and labeling was analyzed by flow cytometry (n=3).

Immunophenotyping

Spleen cell subset of male Balb/c mice, after 30 days of treatment *in vivo* with CPDS, expressed as percentage of total population. Cells were labeled with fluorescent antibodies and labeling was analyzed by flow cytometry (n=8).
* statistically significant

Mitogenic proliferation

Proliferation (cpm) of splenocytes from Balb/c males following exposure to different mitogens: phytohemagglutinin (PHA), concanavalin A (CON A) and lipopolysaccharide (LPS). Animal (n=3) were treated or not with CPDS for 6 days.

Mitogenic Proliferation

Proliferation (cpm) of splenocytes from Balb/c males following exposure to different mitogens: phytohemagglutinin (PHA), concanavalin A (CON A) and Lipopolysaccharide (LPS). Animal (n=8) were treated or not with CPDS for 30 days.

* statistically significant

Humoral response to KLH Immunization

Keyhole limpet hemocyanine (KLH) antibodies quantification in serum of male Balb/C mice following *in vivo* treatment with CPDS for 45 days. Antibody titers were determined by dot blot and converted $\log_2$ of the dilution.

\* statistically significant

METHOD OF IMMUNOMODULATION USING THIONE-FORMING DISULFIDES

CROSS-REFERENCE TO RELATED APPLICATIONS

This application claims the priority benefit of U.S. Provisional application 60/260,943, filed Jan. 10, 2001, which is hereby incorporated by reference in its entirety.

TECHNICAL FIELD

This invention is in the general field of immunology. More specifically, methods of modulating immune responses by using thione-forming disulfides and uses thereof are disclosed. Further, methods of using immunomodulation for therapy are also disclosed.

BACKGROUND OF THE INVENTION

Regulation of the immune system in mammals is complicated and involves many pathways. Various factors can cause a modulation in the immune system, for example, viral infections, bacterial infections, parasitic infections, introduction of drugs or other foreign substances into an individual, transformation of cells into cancerous growths within the individual, and development of autoimmune reactions within the individual. Although the immune system is very complex, it can be divided loosely into three major systems: humoral immunity, cellular immunity, and innate immunity. An important component of the humoral immunity is the B lymphocyte; an important component of the cellular immunity is the T lymphocyte; and an important component of the innate immune system is the NK cell.

The predominant function of B cells is the production of specific antibodies to foreign antigens. Following the interactions of surface receptors with foreign antigens and in the presence of T cells, B cells will differentiate into plasma cells which are the producers of circulating antibodies.

Antigen receptors used by T cells (TCR) are composed of a set of invariant chains (collectively referred to as the CD3 complex) and polymorphic chains divided into constant and variable portions. The T lymphocytes are divided mainly into two subpopulations: the helper T lymphocytes (CD3$^+$CD4$^+$) and the cytotoxic T lymphocytes (CD3$^+$CD8$^+$). The major role of helper T cells is to secrete cytokines that will stimulate other cells to accomplish their functions. The cytotoxic T cells are capable of killing other cells expressing foreign antigens presented in association with major histocompatibility complex I (MHC I) glycoproteins on "accessory cells" such as macrophages.

Compounds have been identified that modulate the immune system. For example, cyclosporin is used to suppress T cells in organ transplantations to prevent rejection of the donor organ by the recipient. Lipopolysaccharides (LPS) have been found to stimulate B cells. Levamisole, an antihelminth agent, has been disclosed to promote phagocytic activity of polymorphonuclear leukocytes. See, for example, Forum on Immunotherapy "The History and Development of Levaminsole", edited by D. A. Willoughby and Clive Wood, Vol. 1 (1):2-10 (1977). 6(5)-phenanthridinone has also been disclosed to inhibit lymphocyte proliferation and depresses induction of CTL cells. Weltin D., et al. *Int. J. Immunopharmac.*, 17(4): 265-271 (1995).

The ability to immunomodulate different populations of cells or even different branches of the immune system can be useful for treating various types of diseases or ailments. Since NK cells are widely known to target tumor cells and virally infected cells, it would be highly beneficial to increase or stimulate NK cells to treat an individual with cancer or with a viral infection(s). In addition to modulating activity or population of cell types, it would also be highly beneficial if a compound could immunomodulate cytokine production, for example, an anti-viral cytokine such as interferon-γ. Further, immunomodulating immune responses such that they would favor a cellular immune response over a humoral immune response could also be beneficial for treating ailments and disease for which cellular immune responses are more effective. Likewise, a shift in immune response from Th2 to Th1 response may be beneficial in avoiding undesired inflammatory responses that may otherwise be encountered during a Th2 response.

There exists a need for compounds that can immunomodulate the cellular, humoral, and innate immune response. The invention disclosed herein fulfulls this need.

All patents, publications, and references referred to herein are hereby incorporated by reference in their entirety.

SUMMARY OF THE INVENTION

Provided herein are methods for immunodulation using thione-forming disulfides (TFDs). In one embodiment, methods for modulating an immune response by administering an effective amount of TFDs to an individual are provided. In another embodiment, methods for immunomodulating a cellular immune response are provided. In this embodiment, the cellular immune response is a T cell response whereby cell populations are increased and/or lymphoproliferative activity is increased. The T cell response (CD4$^+$ or CD8$^+$) can also be specific for a target, such as an HIV-infected cell. In another embodiment, methods for immunomodulating an innate immune response and/or natural killer cell response are provided, for example, increasing the natural killer cell population and NK activity. In yet another embodiment, methods of immunomodulating a humoral immune response are provided. Humoral immune response can be a decrease in B cell population or B cell response, such as antibody secretion. In yet another embodiment, the invention provides for immunomodulation biased towards a Th1-type response. The Th1-type response can be an increased cell population of NK cells or T cells or alternatively, increased activity in NK cells or T cells.

In another embodiment, the invention provides for an increase in cytokine levels (e.g., levels of IL-2, IFN-γ, IFN-α, IFN-β, IL-12, TNF-α, and TNF-β). In another embodiment, the invention provides for an increase in chemokine levels (e.g., RANTES, IL-8, MIP-1α, MIP-1β, MCP-1, lymphotactin, and eotaxin).

In another embodiment, the invention provides for methods of immunomodulation by administering an effective amount of thione-forming disulfides wherein the thione-forming disulfide compound is a dithiobis-heterocyclic compound. The dithiobis-heterocyclic compound can comprise aromatic heterocycles. In another embodiment, the thione-forming disulfide compound has a general formula R-S-S-R, wherein R comprises a heterocyclic aromatic group. In yet another embodiment, the R group comprises a cyclic group having at least one five- or six-membered heterocyclic ring, each heterocyclic ring comprising at least one nitrogen, and optionally further heteroatoms selected from the group consisting of N, O, and S. In yet another embodiment, the R group comprises a pyridinyl, pyrimidinyl, thiazolyl, or quinolinyl group. In yet another embodiment, the five- or six-membered heterocyclic ring comprises negative or potentially negative substituents.

In other embodiments, the invention provides for methods of immunomodulation by administering an effective amount of thione-forming disulfides wherein the compound is 6,6'-dithiodinicotinic acid (CPDS), 6,6'-dithiodinicotinic acid diethyl ester, 4-carboxypyrimidine-2-disulfide, diethyl 2,2'-dithiobis-(4-thiazole carboxylate), or 2,2'-dithiobis-isonicotinic acid.

In another embodiment of the invention, the thione-forming disulfides are administered in a pharmaceutically acceptable carrier.

BRIEF DESCRIPTION OF THE TABLES

Figure 1:
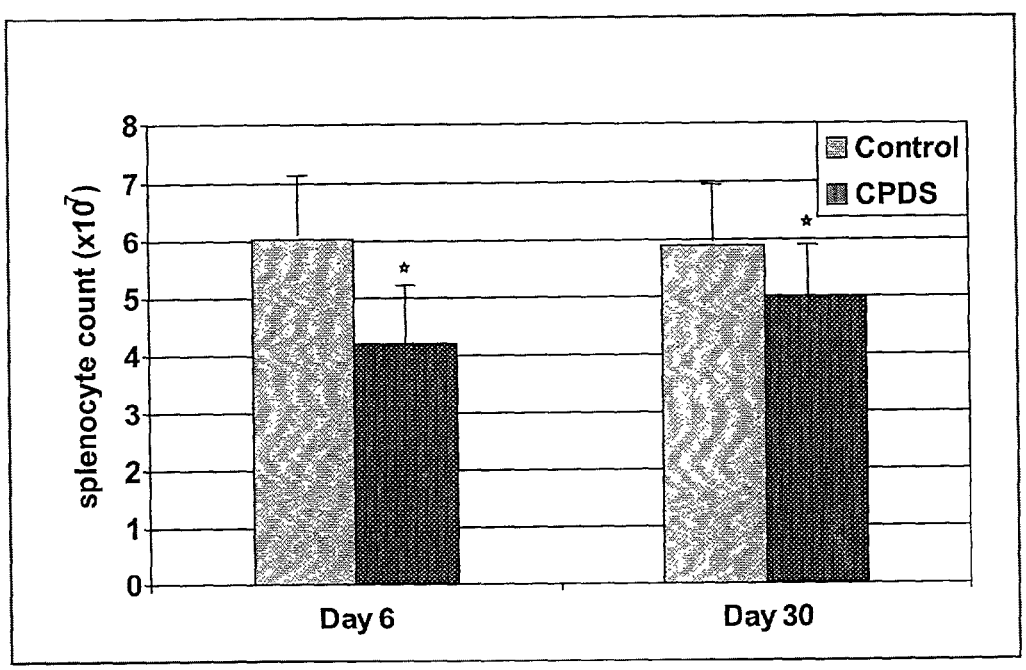
FIG. 1 depicts total splenocyte counts in Balb/c mice after 6 days and 30 days of treatment with CPDS.

Table 1 lists examples of thione-forming disulfides, including salts thereof.

Table 2 lists exemplary useful thione-forming disulfides.

Table 3 depicts the groups of mice which were used for different experiments, the diet used for the experiment, the number of days on the diet, and the type of immunity being tested.

Table 4 depicts the amount of CPDS consumed by the animals during the course of treatment with CPDS.

Table 5 depicts the weigh gain observed in animals fed with CPDS in comparison to animals on a non-CPDS diet.

Table 6 depicts the effect of CPDS on different immune parameters in Balb/c mice after 6 days and 30 days of CPDS treatment.

Table 7 depicts total lymphocyte counts in mice after 6 days and 30 days on normal or CPDS diets.

Table 8 depicts the NK activity, as determined by a standard chromium release assay, in mice after 6 days and 30 days on normal or CPDS diets.

Table 9 depicts the immunophenotyping of T cells, B cells, and NK cells in mice after 6 days and 30 days on normal or CPDS diets.

Table 10 depicts the proliferation ability of lymphocytes from CPDS-treated and untreated mice in response to different mitogens.

Table 11 depicts the humoral response to immunization with keyhole limpet hemocyanin (KLH). The antibody titers are converted to $\log_2$ of the dilution.

DETAILED DESCRIPTION OF THE INVENTION

Provided are methods of immunomodulation by administration of thione-forming disulfides (TFDs) to individuals. In some aspects, the TFDs are administered to immunocompromised individuals to boost their cellular and innate immune responses. In other aspects, TFDs are administered to individuals suffering from one or more viral disease(s) to boost their cellular and innate immune responses. In other aspects, TFDs are administered to individuals with bacterial or fungal infections to amerliorate their condition. In yet another aspect, the TFDs are administered to individuals as a prophylaxis against viral infections or opportunisitic infections.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); *Antibodies: A Laboratory Manual* (Harlow et al., eds., 1987); *Methods of Immunological Analysis* (R. Masseyeff, W. H. Albert, and N. A. Staines, eds., Weinheim: VCH Verlagsgesellschaft mbH, 1993), *Immunobiology* (Janeway, C. A. and Travers, P., 1997); and *Fundamental Immunology* (Paul, W. E., ed., 1999); March, *Advanced Organic Chemistry*, John Wiley & Sons, New York, 1985; and House, *Modern Synthetic Reactions*, The Benjamin/Cummings Publishing Company, Menlo Park, Calif., 1972.

DEFINITIONS

As used herein, "B cells" or "B lymphocytes" are one of two major classes of lymphocytes. B cells are the precursors of antibody secreting cells, plasma cells, and as such are central to the induction of humoral immune responses. The induction of most humoral immune responses in the adult involves a number of cellular interactions among thymus-derived T lymphocytes, commonly called T cells, antigen presenting cells (APC), and B cells (J. Exp. Med 147:1159, 1978; PNAS 77:1612, 1982; PNAS 79:1989, 1982; Immunol. Rev. 95:914, 1987).

As used herein, "T cells" or "T lymphocytes" are a subset of lymphocytes defined by their development in the thymus and by the presence of heterodimeric receptors associated with proteins of the CD3 complex. T cells can be further divided into helper T cells (CD4$^+$ cells) and cytotoxic T cells (CD8$^+$ cells).

"Natural killer cells" or "NK cells" are a class of large lymphocytes which are an important component of the innate immune system.

As used herein, "immune cells" refers to any cells of the immune system including but not limited to T cells, B cells, NK cells, NKT1.1 cells, macrophages, dendritic cells, follicular dendritic cells, neutrophils, eosinophils, basophils, and mast cells.

"Immunomodulation" refers to the modulation of the immune system in response to a stimulus. External stimulus such as a drug, foreign compound, foreign pathogen, or injury can have immunomodulatory effects. In other instances, internal stimulus such as a cancerous transformation or genetic mutation can also have immunomodulatory effects. The effects can be inhibitory, for example, cyclosporin, or activating, for example, glucocorticoids.

An "antibody" (interchangeably used in plural form) is an immunoglobulin molecule capable of specific binding to a target, such as a carbohydrate, polynucleotide or polypeptide, through at least one antigen recognition site, located in the variable region of the immunoglobulin molecule. As used herein, the term encompasses not only intact antibodies, but also fragments thereof (such as Fab, Fab', F(ab')$_2$, Fv), single chain (ScFv), mutants thereof, fusion proteins comprising an antibody portion, humanized antibodies, and any other modified configuration of the immunoglobulin molecule that comprises an antigen recognition site of the required specificity.

An "effective amount" is an amount sufficient to effect beneficial or desired results including clinical results. An effective amount can be administered in one or more administrations by various routes of administration. An effective amount of TFDs described herein in one embodiment is an amount sufficient for a desired immunomodulation, for example, altering the parameters of the cellular and humoral immune system. The alteration can be, for example, in the form of increasing or decreasing certain populations of cells (e.g., T cells, NK cells, B cells, etc.), increasing or decreasing functional activity of immune cells, or activating or repressing immune cells (e.g., switch from $G_0$ to $G_1$ or switch on/off of signaling cascade). In terms of treatment, an "effective amount" of TFDs described herein is an amount sufficient to palliate, ameliorate, stabilize, reverse, slow or delay progression of a disease. In addition, it also includes an amount sufficient to palliate, ameliorate, stabilize, reverse, slow or delay progression of a uncomfortable or undesirable physiological state suffered by an individual.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Th1 response" or "Th1-type response" or "Th1-like response" refers to an immune response which favors optimal cellular immunity. Generally, the production of IFN-γ and macrophage activation are involved.

"Th2" response" or "Th2-type response" or "Th2-like response" refers to an immune response which favors optimal humoral immunity. Generally, class switching of antibodies to all classes is involved.

As used herein, "treatment" is an approach for obtaining beneficial or desired results including and preferably clinical results.

An "individual" is a vertebrate, preferably a mammal, more preferably a human. Mammals include, but are not limited to, farm animals, sport animals, pets, primates, mice and rats.

As used herein, "essentially pure" and "substantially pure" CPDS or thione-forming disulfides (TFDs) refers to a composition which is comprised at least about 80% CPDS or TFDs, for example at least about 85%, or at least about 85%, or at least about 90% CPDS or TFDs, or at least about 95%, or at least about 98% or more.

As used herein, the singular form "a", "an", and "the" includes plural references unless indicated otherwise. For example, "an" antibody includes one or more antibodies.

"Comprising" means including.

Components of the Immune System

The immune system is comprised of multiple types of immune cells and multiple pathways of recognition and activation. Lymphocytes are one type of immune cell. B cells are one of two major classes of lymphocytes. B cells are generated in the fetal liver and continue to develop after birth in the bone marrow. B cells have been described to undergo several stages of development from being a pro-B cell to early pro-B cell to late pro-B cell to large pre-B cell to small pre-B cell to immature B cells and finally to a mature B cell. B cells undergo VDJ recombination/re-arrangement during the earlier stages of development. B cells are further characterized by having an antigen receptor which is comprised of a rearranged immunoglobulin molecule with two heavy and two light chains complexed with the signal transduction molecules Igα and Igβ. During development, B cells can be subject to selection for self-tolerance and the ability to survive in the periphery (outside of the bone marrow). Upon entering the periphery, B cells are considered "naïve" until a specific antigen is encountered which binds to the antigen receptor and activates the B cell. Generally, the immunoglobulin is IgM until an antigen is encountered and then the B cell can undergo isotype switching to IgG, IgA, IgD, IgE, or remain IgM. The B cell then expands clonally to yield many more B cells of the same antigen specificity and the B cells begin secreting antibodies, at which time the B cells can also be called "plasma cells".

T cells are a subset of lymphocytes defined by their development in the thymus and by the presence of heterodimeric receptors associated with proteins of the CD3 complex. Most T cells have α:β heterodimeric receptors, however, some T cells do have γ:ε heterodimeric receptors. The α:β heterodimer is usually associated with εγ and εγ and ζζ complexes (transmembrane proteins) to form the TCR:CD3 complex. T cells are generally divided into helper T cells (CD4$^+$ cells) and cytotoxic T cells (CD8$^+$ cells). Helper T cells assist B cells in making antibodies in response to an antigenic challenge. Some helper T cells can be further delineated as Th2 helper T cells which make IL-4 and IL-5 that drives the Th2 response. Others can be delineated at Th1 helper T cells which make IFN-γ that drives a Th1 response. CD4$^+$ cells recognize their target via major histocompatibility complex II (MHC II) while cytotoxic T cells (CD8$^+$ cells) recognize their targets via MHC class I.

Natural killer cells or NK cells are a class of large lymphocytes (CD3$^+$CD56$^+$ in humans) and are an important component of the innate immune system. NK cells are different from T cells in that their recognition for targets is non-MHC restricted. NK cells represents one of the first lines of defense against foreign antigens and do not require prior exposure to the foreign antigens to become activated, thus, NK cells can act upon foreign pathogens faster than T cells or B cells which require activation and in some cases, isotype switching and proliferation. NK cells can mediate cytotoxity upon binding to the target via NK receptors (e.g., NKR-1, KIR, Ly49) by releasing granules which cause the target cell to undergo apoptosis. NK cells can also mediate cytotoxity via a mechanism called antibody dependent cellular cytotoxity (ADCC). ADCC is the killing of antibody-coated target cells by cells with Fc receptors that recognize the Fc region of the bound antibody. NK cells have FcγRIII receptors that recognize the Fc portion of an antibody. NK cells are thought to target tumor cells and virally infected cells. It has been disclosed that virally infected cells downregulate MHC class I upon infection of a host cell to evade CTL detection by the host's immune system. Since MHC class I is an inhibitor of NK recognition, the act of downregulating MHC class I by the virally-infected cells may make the infected cell a better target for NK recognition.

NKT1.1 cells or NKT cells or NK1.1 CD4 T cells are a small subset of T cells which express the NK1.1 marker, CD56, and α:β T cell receptors of a limited variety and sometimes CD4. NKT cells are major producers of IL-4 early in the immune response.

The many types of immune cells interact in various pathways which involve positive and negative feedback mechanisms. The introduction of a compound, such as thione-forming disulfides, can modulate the immune response.

Thione-Forming Disulfides

Thione-forming disulfides may be used in the methods of the invention. Thione-forming disulfides are disulfides that, upon reaction, for example with a thiol, give rise to a thione. The thione-forming disulfides generally react with thiols or sulfhydryl groups in an essentially irreversible reaction to give as products, a disulfide and a thione. The thione-forming disulfide may initially form a thiol, which tautomerizes to thione. The thione preferably does not equilibrate with the disulfide product. This reaction is exemplified below for the reaction of 6,6'-dithiodinicotinic acid with two thiol groups, R'SH, to produce two thiones and a disulfide product:

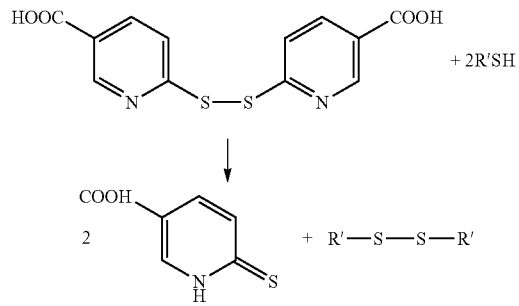

The thione-forming disulfides are, for example, dithiobis-heterocyclic compounds, optionally comprising aromatic heterocycles. The heterocyclic moiety can include, for example, 1 to 5 nitrogen atoms and optionally a further heteroatom, such as sulfur or oxygen, in the ring. The compound may comprise, for example, a cyclic group having at least one five- or six-membered heterocyclic ring, each heterocyclic ring comprising nitrogen, and optionally further heteroatoms such as N, O, or S. The dithiobis-heterocyclic compound may comprise, for example, a pyridinyl, pyrimidinyl, thiazolyl, or quinolinyl heterocyclic group. The heterocyclic group can be substituted or unsubstituted.

The heterocyclic ring can comprise, for example, negative or potentially negative substituents, such as carboxyls, carboxylic esters, amides, sulfate, sulfonate or phosphate groups, or salts of any of the foregoing, or nitro groups.

The thione-forming disulfides in one embodiment may be represented by the general structure:

R-S-S-R, where R is organic moiety, and wherein R can be the same or different organic moiety. Thus, optionally the compound is a mixed disulfide.

In one embodiment, the disulfide compounds are dithiobis-heterocyclic compounds R-S-S-R, wherein R comprises a heterocyclic aromatic group. In one embodiment, R comprises a cyclic group having at least one five or six membered heterocyclic ring, each heterocyclic ring comprising one nitrogen and optionally additional heteroatoms, such as N, O, or S. R also can comprise single or fused rings, such as pyridine, pyrimidine, thiazole, oxazole, dithiouracil, 6-thioguanine, 6-mercaptopurine, quinoline, isoquinoline, quinazoline, quinoxaline and picoline.

In a further embodiment, R comprises heterocyclic rings which may include negative or potentially negative substituents, such as carboxyl, carboxylic esters, amides, sulfate, sulfonate or phosphate groups, or salts of any of the foregoing, such as sodium salts, as well as nitro groups.

In another embodiment, R is an unsubstituted or substituted pyridyl group, optionally substituted by anionic groups, alkyl groups, hydroxyl, —CN, halogen, CNO, carboxyl, ester, or amide groups.

In one embodiment, the thione-forming disulfides contain one of the following partial structures, a vinyl (—C=N—) type or a vinylidene (—C=C—C=N—) type structural fragment, and is proximally linked to a disulfide moiety, as represented in Scheme I, wherein X and Y represent atoms necessary to form a five- or six-membered substituted or unsubstituted heterocyclic ring and optionally fused to a substituted or unsubstituted carbocyclic or heterocyclic ring, permitting the formation of a thione, as indicated below in Scheme I:

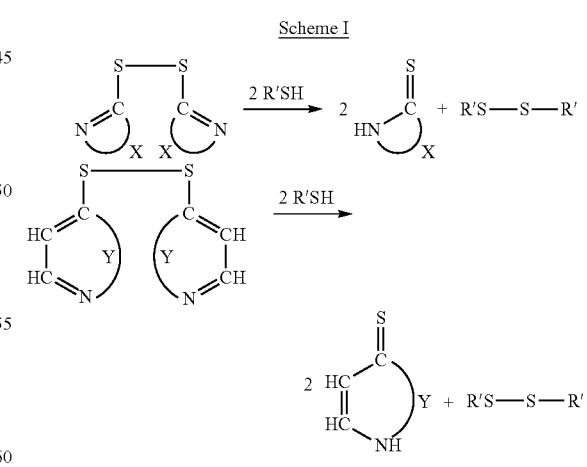

An example of a thione-forming disulfide is 6,6'-dithiodinicotinic acid (or carboxypyridine disulfide). In one embodiment, R comprises various substituted pyridyl or pyrimidyl moieties, with substituents including a carboxy group or salt form thereof, and/or ester and amide derivatives of the carboxy group.

Salt forms of any of the compounds may be used. Suitable salts are, for example, those that form with alkali or alkaline earth metals, with ammonia or with amines such as cyclohexylamine, morpholine or other aliphatic, alicyclic, aromatic or heterocyclic amines. Salts include sodium, potassium, magnesium, and ammonium salts.

Suitable substituents which may be present on heterocycles of the disulfide compounds include ester moieties including methyl, ethyl and higher alkyl groups, cyclohexyl and other alicyclic groups. Suitable amide moieties include —CONR'R", wherein, R' and R" are independently H, aliphatic, heterocyclic, alicyclic or aromatic groups and substituted derivatives thereof.

The pyridine ring in 6,6'-dithiodinicotinic acid is merely one of the many possible thione-forming disulfides. Other heterocyclic aromatic moieties include quinolinyl, pyrimidinyl and thiazolyl groups and substituted derivatives thereof, including various salt forms such as sodium, potassium, ammonium or magnesium salts. Non-limiting examples of thione-forming disulfides, including salts thereof, such as sodium salts, are listed in Table 1.

TABLE 1

Pyridine Derivatives 6,6'-dithiodinicotinic acid
6,6'-dithiodinicotinic acid diethyl ester
2,2'-dithiobis-isonicotinic acid
2,2'-dithiobis-(5-acetamidopyridine)
6,6'-dithiodinicotinamide
2,2'-dithiodipyridine
4,4'-dithiodipyridine
2,2'-dithiobis-(5-aminopyridine)
2,2'-dithiobis-(5-cyanopyridine)
2,2'-dithiobis-(5-nitropyridine)
2,2'-dithiodipyridine-di-N-oxide Quinoline Derivatives 2,2'-dithiodiquinoline Pyrimidine Derivative 4-carboxypyrimidine-2-disulfide
2,2'-dithiodipyrimidine
2,2'-dithiobis-(4-methylpyrimidine)

Thiazole Derivative diethyl 2,2'-dithiobis-(4-thiazole carboxylate)
2,2'-dithiobis-(5'-methylthiazole)
2,2'-dithiobis-benzothiazole Thione forming disulfides described in the art may be used, for example, those described in U.S. Pat. No. 3,698,866; U.S. Pat. No. 3,597,160; U.S. Pat. No. 4,378,364; U.S. Pat. No. 4,152,439; U.S. Pat. No. 6,043,256; PCT WO 99/07368; Canadian Patent No. 985170; Grassetti, D. R. *Cancer Letters*, 31:187-195 (1986); Grassetti, D. R. *Nature*, 308(5959): 500 (1984); and Grassetti, D. R. *Nature*, 228(268):282-283 (1970), the disclosures of which are incorporated herein by reference in their entirety.

Exemplary useful thione-forming disulfides include the following compounds:

6,6'-dithiodinicotinic acid:

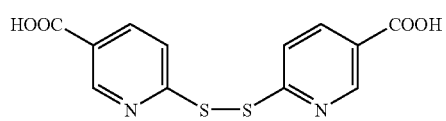

6,6'-dithiodinicotinic acid diethyl ester:

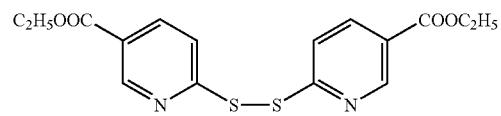

2,2'-dithiobis-isonicotinic acid:

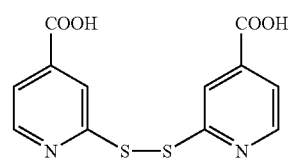

4-carboxypyrimidine-2-disulfide:

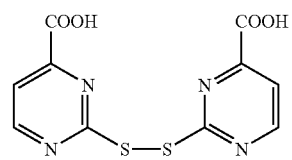

and diethyl 2,2'-dithiobis-(4-thiazole carboxylate):

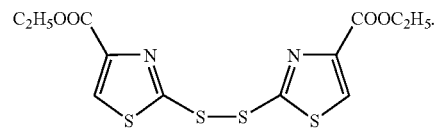

Other non-limiting examples include the compounds, including salts thereof, such as sodium salts, listed in Table 2:

TABLE 2

6,6'-dithiodipicolinic acid
4,4'-dithiodipicolinic acid
4,4'-dithiodinicotinic acid
2,2'-dithiodinicotinic acid
4,4'-dithiobis(2,5-pyridinedicarboxylic acid)
4,4'-dithiobis(2,6-pyridinedicarboxylic acid)
4,4'-dithiobis-(2,6-pyridinedicarboxylic acid)
2,2'-dithiobis-(3,4-pyridinedicarboxylic acid)
4,4'-dithiobis-(3,5-pyridinedicarboxylic acid)
4,4'-dithiobis-(2,3,5-pyridinetricarboxylic acid)
2,2'-dithiobis-(3,4,5-pyridinetricarboxylic acid)
2,2'-dithiobis-(3,4,5,6-pyridinetetracarboxylic acid)

The synthesis of these disulfides can be often carried out by oxidation of the corresponding thiol with hydrogen peroxide, or iodine-potassium iodide under neutral conditions.

The thione forming disulfide compounds are available commercially or synthesized from commercially available compounds. Examples of methods for the syntheses of disulfide compounds, and commercial sources are as follows.

6-Mercaptonicotinic acid (6MNA) is prepared according to Rath, C., *Justus Liebigs Ann. Chem.*, 487, 95-106, (1931), and also is commercially available from Sigma-Aldrich, St. Louis, Mo. 6,6'-Dithiodinicotinic acid (CPDS) is prepared as described by Grassetti et al., *J. Med. Chem.*, 10: 1170-1172 (1967), and also is available commercially from different sources, such as Sigma-Aldrich (St. Louis, Mo.); Galantis S. P. A., Via delle Industrie, 11, 30020, Marcon Venezia Italy; and Chemsyn Laboratories, 13605 W. 96th Terrace, Lenexa, Kans. 66215-1297.

The diethyl ester of 6,6'-dithiodinicotinic acid may be prepared as described by Grassetti, D. R., *Cancer Lett.*, 31, 187-195 (1986). 4-Carboxypyrimidine-2-disulfide may be obtained by the oxidation of 2-mercapto-4-pyrimidine carboxylic acid, which may be prepared according to Daves et al., *J. Herocyclic Chem.*, 23, 130-133(1964). The oxidation may be carried out according to the method of Fox and Gibas, *J. Org. Chem.*, 23, 64-66 (1958). Diethyl 2,2'-dithiobis-4-thiazole carboxylate may be obtained by oxidation of ethyl 2-mercapto-4-thiazole carboxylate, and may be prepared according to D'Amico and Bartram *J. Org. Chem.*, 25, 1336-1342 (1960). Isonicotinic acid is available commercially from Aldrich-Sigma (St. Louis, Mo.). See also, for example, Grassetti, D. R. et al. *Journal of Medicinal Chemistry* 9: 149 (1966); Grassetti, D. R. et al. *Journal of Medicinal Chemistry* 10: 1170 (1967); and Grassetti, D. R. et al. *Journal of Medicinal Chemistry* 13: 273 (1970).

While not being limited to any theory, possible mechanisms of action of the thione-forming disulfide compounds include reaction of sulfhydryl groups on cell surfaces; modifying cellular surface interactions; and effects on the activity of the chromatin-bound enzyme, poly (ADP-ribose) synthetase. See, e.g., Purnell, M. R. and Whish, W. J. D., *Biochem. J.*, 85, 775-777 (1980); and Grassetti, D. R., *Cancer Letters*, 187-195 (1986)).

Some thione forming disulfide compounds, such as CPDS, have been shown to have low toxicity. Grassetti, D. R., *Cancer Letters*, 31: 187 (1986); Boot, J. H., *Cell Structure and Function*, 20: 233 (1995); Grassetti, D. R., *Drugs of the Future*, 11: 559 (1986); U.S. Pat. No. 4,378,364; Grassetti D. R. and Murray, J. F., *Biochem Pharmacol*. 17(11):2281-90 (1968); and Grassetti D. R. and Murray, J. F., *Biochem Pharmacol*. 16(12):2387-93 (1967). Preferred are thione forming disulfides with low toxicity.

Pharmaceutical Compositions

The disulfide compounds, including salts thereof, are optionally provided in a pharmaceutically acceptable form with a pharmaceutically acceptable carrier, for example in a pharmaceutical dosage form. Pharmaceutical organic or inorganic carriers can be used.

Preferred pharmaceutically acceptable salts are salts which retains the activity of the parent compound and do not impart any deleterious or untoward effect on the subject to which it is administered and by the context in which it is administered.

Preferred pharmaceutically acceptable carriers are those which do not cause an intolerable side effect, but which allow the thione-forming disulfide compound to retain its pharmacological activity in the body.

Formulations for parenteral and nonparenteral drug delivery are known in the art and are set forth in *Remington's Pharmaceutical Sciences*, 18th Edition, Mack Publishing (1990).

For solid compositions, conventional non-toxic carriers include, for example mannitol, lactose, starch, magnesium stearate, magnesium carbonate, sodium saccharin, talcum, cellulose, glucose, sucrose, pectin, dextrin, tragacanth, methyl cellulose, sodium carboxymethyl cellulose, a low-melting wax, cocoa butter, and the like may be used. The active compound as defined above may be formulated as suppositories using, for example, polyalkylene glycols, for example, propylene glycol as a carrier.

A solid carrier can be one or more substances which may also act as diluents, flavoring agents, solubilizers, lubricants, suspending agents, binders, or tablet disintegrating agents; it can also be an encapsulating material. In a similar manner, cachets or transdermal systems are included. In powders, the carrier is a finely divided solid which is in a mixture with the finely divided active component. In tablets, the active component is mixed with the carrier having the necessary binding properties in suitable proportions and compacted in the shape and size desired.

Liquid form preparations include solutions, suspensions, or emulsions suitable, for example, for oral administration. Aqueous solutions for oral administration can be prepared by dissolving the active compound in water and adding suitable flavorants, coloring agents, stabilizers, and thickening agents as desired. Aqueous suspensions or emulsions for oral use can be made by dispersing the finely divided active component in water together with a viscous material such as natural or synthetic gums, resins, methyl cellulose, sodium carboxymethylcellulose, and other suspending agents known to the pharmaceutical formulation art. If desired, the pharmaceutical composition to be administered may also contain minor amounts of non toxic auxiliary pH buffering agents and the like, for example, sodium acetate, sorbitan monolaurate, triethanolamine oleate, etc. Actual methods of preparing such dosage forms are known, or will be apparent to those skilled in this art; for example, see Remington's Pharmaceutical Sciences. The composition or formulation to be administered will preferably contain a quantity of the active compound in an amount effective to alleviate the symptoms of the subject being treated.

Parenteral administration is generally characterized by injection, whether subcutaneously, intramuscularly, or intravenously. Injectables can be prepared in conventional forms, either as liquid solutions or suspension, solid forms suitable for solution or suspension in liquid prior to injection, or as emulsions. Suitable excipients include, for example, water, saline, aqueous dextrose, glycerol, ethanol or the like. In addition, if desired, the pharmaceutical compositions may also contain minor amounts of non-toxic substances such as wetting or emulsifying agents, auxiliary pH buffering agents and the like, for example, sodium acetate, sorbitan monolaurate, triethanolamine oleate, etc.

The pharmaceutical preparation may be in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The optimal effective concentration of thione-forming disulfides can be determined empirically and will depend on the type and severity of the disease, route of administration, disease progression and health and mass or body area of the patient. Such determinations are within the skill of one in the art.

Administration of Thione-Forming Disulfides

Various formulations of thione-forming disulfides (TFDs) may be used for administration. In one embodiment, the thione-forming disulfide is CPDS. In another embodiment, the CPDS is administered orally. The oral administration can be a capsule form or by dissolving CPDS powder in an aqueous solution for consumption (e.g., water). To make a capsule form, an effective amount of TFD, such as CPDS, can be admixed with a solid or viscous ingredients disclosed supra. In another embodiment, the CPDS is mixed with food which the individual will be ingesting. In the case of pets such as cats, the CPDS may be mixed with the cat chow by grinding up the cat chow, mixing with the CPDS and then re-forming the cat chow in a pellet-size form.

These compositions may be formulated for administration by injection (e.g., intraperitoneally, intravenously, subcutaneously, intramuscularly, etc.). Accordingly, these compositions are for example combined with pharmaceutically acceptable vehicles disclosed supra. For example, the TFDs can constitute about 0.01% to 50% by weight of the formulation depending upon practical or empirical considerations such as solubility and osmolarity. The particular dosage regimen, e.g., dose, timing and repetition, will depend on the particular individual and that individual's medical history. Dosage examples include a dose of about 10 μg to about 5 g TFD/kg body weight, or about 500 μg to about 900 mg/kg body weight, or about 1 mg to about 500 mg/kg body weight, or about 50 mg to about 250 mg TFD/kg body weight. Empirical considerations, such as the half life, generally will contribute to determination of the dosage. Other dosages, such as about 10 mg to 250 mg, e.g., 140 mg daily, are possible over a daily, weekly, monthly, or yearly dosing regimen.

The purity of thione-forming disulfides may be an important factor for determining toxicity to an individual taking TFDs. For example, the purity is at least about 75%, or at least about 80%, or at least about 85%, or at least about 90%, or at least about 95%, or at least about 99%. For example, the purity may be 98.2%, 98.4%, 98.6%, or 98.8%. Some TFDs are sensitive to light, and therefore it is preferred that these TFDs be protected from light, for example, during storage.

The frequency of administration may be determined and adjusted over the course of therapy, and can be based on immune cell counts (NK cells, T cells, etc.) or physical health (e.g., maintaining a sense of well-being). Other appropriate dosing schedules may be as frequent as multiple doses daily or 3 doses per week, or one dose per week, or one dose every two to four weeks, or one dose on a monthly or less frequent schedule depending on the individual. The dosing regimen can be sustained for a week, two weeks, a month, three months, six months, one year, or, for example, ten years. Sustained continuous release formulations of the compositions may be appropriate. Various formulations and devices for achieving sustained release are known in the art.

Other formulations include those suitable for topical administration, which may be suitable if the thione-forming disulfides are able to cross the mucosa. Topical administration can be achieved by combining the TFD, for example, CPDS, with one or more ingredients that are suitable for topical administration. Possible ingredients include, but are not limited to, petroleum jelly, glycerin, and any commercially available lip ointment. The amount of TFD such as CPDS can vary from treatment to treatment, however, an effective amount of CPDS is combined with ingredients suitable for topical administration.

Other formulations include suitable delivery forms known in the art including, but not limited to, aerosol formulations and carriers such as liposomes. Mahato et al. (1997) *Pharm. Res.* 14:853-859. Liposomal preparations include, but are not limited to, cytofectins, multilamellar vesicles and unilamellar vesicles.

In some embodiments, more than one thione-forming disulfide may be present in a composition. Such compositions may contain at least one, at least two, at least three, at least four, at least five different thione-forming disulfides. Such "cocktails", as they are often denoted in the art, may be particularly useful in treating a broader range of population of individuals. They may also be useful in being more effective than using only one (or fewer than are contained in the cocktail) thione-forming disulfide(s). Further, a "cocktail" of thione-forming disulfides can be used to treat one disease (e.g., AIDS) or multiple diseases (e.g., AIDS and influenza). In the alternative, a "cocktail" may be used to treat one disease which is in a more advanced state of progression. State of disease will vary accordingly depending on the disease. For viral diseases, titer of virus can be measured to determine the progression or alternatively, in immune-related diseases, the antibody titer to the virus may be measured. For AIDS, the number of $CD4^+$ cells can be measured or CD4/CD8 cell ratio to determine progression of AIDS.

The compositions may be administered alone or in conjunction with other forms of agents that serve to enhance and/or complement the effectiveness of a thione-forming disulfide of the invention, including, but not limited to, antibiotic treatments. Such treatments usually employ agents that suppress bacterial infection and growth. Other agents are fungicidal treatments.

Administration of TFD or CPDS is in an amount which is not toxic to the individual. Toxicity may be determined by a stepwise increment of dosage and monitoring survival rates, self-described state of physical health, or monitoring blood contents for indices of toxic response.

Uses of Thione-Forming Disulfides in Immunomodulation

Thione-forming disulfides may be used to increase or decrease specific immune cell populations. If an increased NK cell population is desired, one or more TFD(s), such as CPDS, is given to an individual in an effective amount. Similarly, if increased NK activity is desired, one or more TFD(s), such as CPDS, is given to an individual in an effective amount. If an increase in T cell population and activity is desired, one or more TFD(s), such as CPDS, is given to an individual in an effective amount. Administration of TFDs may help enhance NK cell activity and T cell activity in addition to other immune cells involved in the cellular immune response. Phagocytic ability of macrophages may improve with the administration of one or more TFD(s) and increased phagocytic ability of macrophages can lead to more efficient clearance of foreign matter invading the individual's body.

In addition, the phagocytosed matter can be presented on more macrophages in greater amounts and this leads to greater immune stimulation potential by the engagement of the helper T cells. The helper T cells and CTL cells are activated and the T cells in turn engage in a positive feedback loop which further perpetutates their activation state and enhances their activity, growth, proliferation, and/or survival. Further, the macrophage secretes IL-12 which stimulates NK cells. A series of reactions occur within the cellular immune response which serve to positively enhance activity and growth.

Another use for TFD(s) is to modulate the cytokine or chemokine response. Activated NK cells secrete IFN-γ which in turn activates CTL cells and can feedback to activate other immune cells such as helper T cells. Other activated cells of the cellular immune system can modulate the secretion of cytokines and chemokines. The cytokines and chemokines can have an anti-viral effect, as in the case of IFN-γ, IFN-α, IFN-β, TNF-α, or TNF-β, or serve to recruit other cells to the local area, as in the case of RANTES. The mobilization of cytokines and chemokines may aid in treating viral infections, such as HIV, the common cold, and influenza. In another embodiment, the mobilization of cytokines and chemokines may aid in preventing viral infections, such as HIV, the common cold, and influenza.

Another use for TFD(s) in the immunomodulation of an individual is that an immune response may be biased toward Th1 or Th2 response. The response may be Th1-type response if an optimal cellular response is desired. In the case of viral infections where a cellular immune response with a Th1 bias would be more useful, an effective amount of CPDS or any other TFD would be administered to achieve the Th1 response. In another embodiment, the response may be a Th2 response if an optimal humoral response is desired. In another embodiment where an inflammatory response and/or a Th2-type response is not desired, an effective amount of CPDS or TFD(s) is administered to favor a Th1-type response and to reduce the bias towards a Th2-type response. CPDS or TFD(s) may also be used to immunomodulate B cell population (e.g., reduce antibody levels), as exemplified in Example 6 and Table 4. Reduction of antibody levels are useful in some circumstances, for example, to avoid and/or prevent complication arising from immune complexes, for example, renal failure in systemic lupus erythmatosus, bacterial endocarditis, or serum sickness.

Immunomodulation in Treatment of Diseases and Other Ailments

TFDs can be used to immunomodulation to treat a variety of diseases and other ailments. Optionally, a baseline of immune system components and function is obtained before the administration of TFDs. In the alternative, measurements of the immune cell population and their functionality is obtained after the administration of TFDs and may be later monitored to assess efficacy of TFDs treatment. Diseases and ailments which can be treated include but are not limited to: viral infections (e.g., influenza virus, Epstein Barr virus, rhinovirus, adenovirus, retrovirus, lentivirus, human immunodeficiency virus, feline immunodeficiency virus, cytomegalovirus, measles virus, herpes virus, varicella zoster virus, hepatitis virus, echovirus, etc.), common cold, AIDS, pneumonia, bacterial infection, Candidiasis, infection with *Candida* species (e.g., *candida albans*), mycosis, ataxia telangiectasia, and fungal infection.

TFDs can also be used to boost immune response in immunocompromised individuals, e.g., patients undergoing chemotherapy or individuals with genetic defects of immune function or the elderly. Patients undergoing chemotherapy may have lower than normal numbers of immune cells and the immune cells which are present may have had their functional activity compromised by the chemotherapy. In this case, it is beneficial to administer one or more TFD(s) to patients who are undergoing or have had chemotherapy treatment to boost their immune cell populations and functions.

Other individuals who are immunocompromised for other reasons (e.g., AIDS, genetic, etc.) are vulnerable to many infectious agents. These infectious agents include but are not limited to mycobacteria, *Salmonella, Listeria*, all fungi, more commonly found *Candida* species, *Cryptococcus neoformans*, and parasites (e.g., *P. carinii, Toxoplasma gondii, Cryptosporidium, Isospra belli, Strongyloides stercoralis*). Administration of TFD which can immunomodulate and boost the immune system can not only treat state of immunosuppression but also act as a prophylatic means to prevent secondary infections by the infectious agents listed above.

Methods of administering TFDs are disclosed supra. One embodiment for general medicaments is oral administration, either in capsule form or ingestion with food or beverage. For treatment of viral infections (e.g., influenza, AIDS, FIV), baseline measurements of immune parameters (e.g., absolute numbers of T cells, NK cells, B cells, neutrophils, macrophages, activation state of these cells, factors being secreted, etc.) may be taken prior to administration of TFDs. After administration of TFDs and during the course of treatment, immune parameters are monitored periodically to determine how effective the TFD is for treatment. The dosage and timing of administration will vary from treatment to treatment, however, by monitoring immune parameters, a skilled artisan can easily adjust the dosage (e.g., increasing or decreasing incrementally) or the timing (e.g., change from one dose daily to two doses daily) to achieve immunomodulation. Depending on if the ailment or disease is chronic, the medicament regimen may run a course of a few weeks to a few years. If the ailment is localized, for example a cold sore which may or may not be associated with herpesvirus infection, a preferred embodiment of the invention is a topical remedy in which one or more TFD(s), such as CPDS, is admixed with one or more ingredients which are suitable for topical administration to site of the cold sore(s). For bacterial or fungal infection such as mycosis which has multiple physical manifestation, a combination of topical and oral medicament of one or more TFD(s) can be used for treatment.

Methods of Monitoring Immunomodulation and Determining Efficacy of TFDs

Detection and measurement of immunomodulation are generally based on measurement of various biological factors in the individual taking TFDs. Samples may or may not be obtained from the individual before the administration of the TFD for a baseline measurement. Samples may be taken after administration of TFD at intervals to monitor the effect(s) of the TFD on the individual. Samples of blood may be taken from individuals and assessed for numbers of various immune cells. Blood drawn from an individual can be analyzed on a flow cytometer or the blood may be layered over a sucrose gradient or other types of gradients (e.g., Percoll® or Ficoll®) to isolate white blood cell population.

In another embodiment, samples are obtained from cell culture or frozen tissue samples from individuals to whom TFDs have been administered. The cells from the cell culture or frozen tissue samples can be analyzed for efficacy of TFDs on immunomodulation as described below. The samples may or may not be monitored prior to administration of TFDs to the cells.

Antibodies against markers specific for specific immune cell populations can be used to delineate specific populations. To monitor T cell population, CD3, CD4 and CD8 are suitable markers to delineate the T cell population. To delineate helper T cell population, CD3 in combination with CD4 may be used and the percent $CD3^+CD4^+$ cells are multiplied by total cells to obtain an absolute number. To delineate cytotoxic T cell population, CD3 in combination with CD8 may be used and the percent $CD3^+CD8^+$ cells are multiplied by total cells to obtain an absolute number. To delineate NK cell population, in humans, CD3 in combination with CD56 may be used and the percent $CD3^-CD56^+$ cells are multiplied by total cells to obtain an absolute number. To delineate B cell population, CD19, CD20, CD21, CD22, or CD23 alone or in combination with other B cell markers may be used and the percent $CD19^+$, $CD20^+$, or $CD21^+$, $CD22^+$, or $CD23^+$ cells are multiplied by total cells to obtain an absolute number. The antibodies specific for markers on immune cells are easily obtainable from any number of commercial sources such as Becton Dickinson (San Jose, Calif.) or Beckman Coulter (Palo Alto, Calif.). The antibodies can be obtained directly conjugated to a fluorochrome or unconjugated in which case indirect staining with a second antibody which has the capacity to be visualized is used. Possible fluorochromes which can be used for direct or indirect staining of cells include but are not limited to fluorescein isothiocyanate (FITC), phyto-erythrin (PE), PE-Cy5, PerCP, and APC. In the disclosed manner, population of immune cells may be monitored to determine if the administration of TFDs or CPDS is increasing or decreasing a population of immune cells.

Activation state of immune cells can be monitored by several methods. One method is to detect the presence of activation markers on immune cells. Examples of markers which may be used to detect activation state include but are not limited to CD25 and CD69. Another method of detecting activation is staining by immunohistochemistry. Cell surface markers or intracellular protein (e.g., lytic granules) indicative of activation state can be detected with immunohistochemistry.

Another method of monitoring immunomodulation is by monitoring activity (e.g., functional activity, proliferative activity, etc.). Examples of assays which test functional activity include standard chromium release assay for NK cells and CTL cells. In these assays, appropriate target cells are labeled with chromium and combined with the effector cells of interest (NK cells or CTL cells) and the lytic capacity of the effector cells are measured by chromium release of the target cells. It is to be understood that the proper controls (e.g., maximal release and spontaneous release) are undertaken to ensure the most reliable measurements. Generally, the percent specific lysis is calculated by [(experimental release−spontaneous release)/(total release−spontaneous release)]× 100. The selection of appropriate target cells will vary depending the effector cell being tested. For standard NK assays, appropriate target cells include, but are not limited to, K562 cells, U937 cells, and YAC-1 cells. These cells can be obtained through the American Type Culture Collection (ATCC). For standard CTL assays, the target cells should be able to express MHC class I and also be MHC matched for the CTL to recognize the target cells. The MHC class I molecules on the surface of the target cells are filled with peptides for the CTL cells to recognize. The filling of MHC class I molecules with peptides can be accomplished several ways. First, the target cells can be "pulsed" with peptides of a length appropriate for a MHC class I molecule. Generally, the peptides are at least about 5 amino acids in length, more preferably at least about 8 amino acids in length, more preferably at least about 10 amino acids in length, more preferably at least about 12 amino acids in length. The peptides are incubated with the target cells and some peptides are incorporated into empty MHC class I molecules. Other methods of loading MHC class I molecules include infecting the target cell with a virus that expresses the protein which is to be recognized. The protein will then be processed by the target cell's intracellular machinery (e.g., proteasomes) to generate suitable peptides which will then associate with MHC class I molecules in the ER compartment and the complex of MHC class I molecule and peptide is transported to the cell surface. Generally, the virus selected is a virus that is capable of infecting the target cells and also capable of expressing the protein at high levels within the cell. Examples of viruses that may be used for these purposes include, but are not limited to, vaccinia virus, alphavirus, herpes virus, and Epstein Barr virus (EBV).

Another assay which may be used to assess immunomodulation is a standard proliferative assay whereby cells, generally lymphocytes, are grown in the presence of $^3$H-thymidine and the amount of $^3$H-thymidine incorporation is a measurement of the ability of the lymphocytes to proliferate. The lymphocytes can be sorted into specific populations first by flow cytometry, as disclosed supra, or be taken as a population together without sorting.

To monitor humoral immunity, keyhole limpet hemocyanin (KLH) is a strong immunogenic protein very often used to evaluate the capability of an animal to produce antibody. The primary response generally produces antibodies of IgM and IgG type. The measurement of the secreted antibodies can be performed by a dot blot assay, in which the antigen is immobilized on a solid surface and then put in presence of different dilutions of the serums to be tested for antibody quantification. Antigen-antibody complexes are then revealed by a chemoluminescence technique.

Another method of detecting immunomodulation is to measure specific factors secreted by the immune cells by using ELISA (enzyme-linked immunosorbant assay) or ELISPOT assays. Cell are isolated from an individual, as disclosed supra, and cultured in appropriate media. An appropriate, defined medium supporting cell survival maintains the viability, morphology, capacity to metabolize and potentially, capacity of the cell to differentiate. A defined medium also promotes cell growth provides all chemicals necessary for cell proliferation or multiplication.

The general parameters governing mammalian cell survival and growth in vitro are well established in the art. Physicochemical parameters which may be controlled in different cell culture systems are, e.g., pH, $pO_2$, temperature, and osmolarity. The nutritional requirements of cells are usually provided in standard media formulations developed to provide an optimal environment. Standard media can include serum supplementation, for example, fetal calf serum for nutrients. Nutrients can be divided into several categories: amino acids and their derivatives, carbohydrates, sugars, fatty acids, complex lipids, nucleic acid derivatives and vitamins. Apart from nutrients for maintaining cell metabolism, most cells also can require one or more hormones from at least one of the following groups: steroids, prostaglandins, growth factors, pituitary hormones, and peptide hormones to proliferate. In addition to hormones, cells may require transport proteins such as transferrin (plasma iron transport protein), ceruloplasmin (a copper transport protein), and high-density lipoprotein (a lipid carrier) for survival and growth in vitro. The set of optimal hormones or transport proteins will vary for each cell type. Most of these hormones or transport proteins have been added exogenously or, in a rare case, a mutant cell line has been found which does not require a particular factor. A variety of basal nutritional media are commercially available. Non-limiting examples of these minimal culture media include F12/DME, Ham's F10 (Sigma), Minimal Essential Medium (MEM, Sigma), RPMI-1640 (Sigma), Dulbecco's Modified Eagle's Medium (DMEM, Sigma) and Iscove's Modified Eagle's Medium (IMDM). In addition, any of the basal nutritional media described in Ham and Wallace (1979) *Meth. Enz.*, 58:44, Barnes and Sato (1980) *Anal. Biochem.*, 102:255, or Mather, J. P. and Roberts, P. E. (1998) *Introduction to Cell and Tissue Culture*, Plenum Press, New York, can be used. For certain immune cells, one ore more stimulatory factors such as PHA, LPS, or IL-2 may be added to the basal media for optimal culturing conditions.

After the immune cells have been isolated and cultured appropriately, as disclosed supra, the supernatant is collected and used in an ELISA specific for a specific factor, such as interferon-, which is secreted by NK cells. Since interferon-γ promotes a Th1 response, a high level of interferon-γ in the supernatant of cultured cells indicates that the immune response, as a whole, would tend to that of a Th1 response. Other cytokines which may be tested include but are not limited to IL-1, IL-2, IL-4, IL-5, IL-6, IL-12, TNF-α, TNF-β, interferon-α, and interferon-β. In addition to cytokines, other factors such as chemokines (RANTES, IL-8, MIP-1α, MIP-1β, MCP-1, lymphotactin, and eotaxin) may also be tested to monitor immunomodulation. Cytokines and chemokines are also readily detectable within cells by using flow cytometry either with or without permeabilizing detergents. If a permeabilizing detergent is used, preferably the detergent does not lyse the cells (e.g., "gentle" detergent). An example of a "gentle" detergent which may be used is saponin.

The following examples are provided to illustrate but not to limit the invention in any manner.

EXAMPLES

Several studies were conducted to investigate the short term and long term effect of CPDS on the immune system of animals. Six groups of animals were used for subsequent analysis of immune parameters over time. Three groups of adult male BALB/c mice were fed Purina chow containing CPDS for 6, 30 days and 45 days. At the end of the experiment animals were sacrificed and aspects of cellular and humoral immunity were evaluated.

Example 1

Method for Administering CPDS

Thirty-eight adult Balb/c mice were acquired from Charles River and divided into 6 different groups (Table 3).

To prepare a CPDS diet, a total of 3 kilos of Standard Purina chow was reduced to powder using a grinder. About 12 g of CPDS was added to the powder and thoroughly mixed, re-hydrated and reconstituted into pellets. Pellets were allowed to dry overnight.

Male adult BALB/c mice were weighed and randomly divided to form the experimental groups. Mice were allowed to acclimatized 3 days prior to the beginning of the experiments. Mice from the control normal diet groups were fed ad libitum with standard Purina mouse chow. Mice from the CPDS treated groups were fed ad libitum with the CPDS preparation. The amount of food given was weighted and recorded to allow the evaluation of the CPDS dosage.

Table 4 shows food consumption of animals in all the experimental groups. CPDS was incorporated to the regular Purina mouse chow for a ratio of 4 g of CPDS per kg of Purina mouse chow. In group 2 after 30 days, food consumption ranged between 0.45 g and 0.53 g (mean 0.48±0.04 g). In group 4 after 45 days food consumption ranged between 0.47 g and 0.59 g (mean 0.53±0.06 g). In group 6 after 6 days of diet, mice ingested an average of 0.1 g of CPDS.

The weight gained by each mice was evaluated weekly and prior to sacrifice. Mice were sacrificed by overexposure to $CO_2$. The spleen from each mouse was collected under sterile conditions, transferred into HBSS buffered solution and kept on ice until used for other studies disclosed. Experiments were performed on the same day.

Weight gain by the control mice and experimental mice (fed with CPDS) is shown in Tables 5. Weight gain was constant and normal for the groups fed with the CPDS diet for 6 and 30 days. Animal weight in the group fed with CPDS diet for 45 days stabilized after day 35 and no weight gain was observed at day 45 even if food intake was constant for that period. When compared with the group of animals fed with normal Purina mice chow (24.43 g), the group fed with CPDS for 45 days showed a statistically significant lower weight gain (p=0.01432).

The animals in groups 1-6 were then tested for immuno-modulation as described in Examples 2-7.

Example 2

Immunomodulatory Effect of CPDS on Splenocytes

Splenocytes were isolated by obtaining spleen from the sacrificed mice on the same experimental day, homogenizing the spleen using a 50-M mesh screen, and suspending the homogenate in 25 ml of RPMI 1640. The splenocyte suspension was washed and then spun at 1200 rpm for 5 minutes. The red blood cells were lysed by an osmotic choc with distilled water. The splenocyte suspension was washed and spun at 1200 rpm for 5 minutes. The splenocytes were suspended in complete RPMI media (90% RPMI 1640, 10% FBS, antibiotics 1×, HEPES 1 mM) and the suspension was filtered through cotton wool. Cells were counted using trypan blue exclusion method. Total splenocyte count was recorded (Table 7). Cells were kept on ice and diluted to the appropriate concentration for the corresponding experimental procedures.

Figure 4:
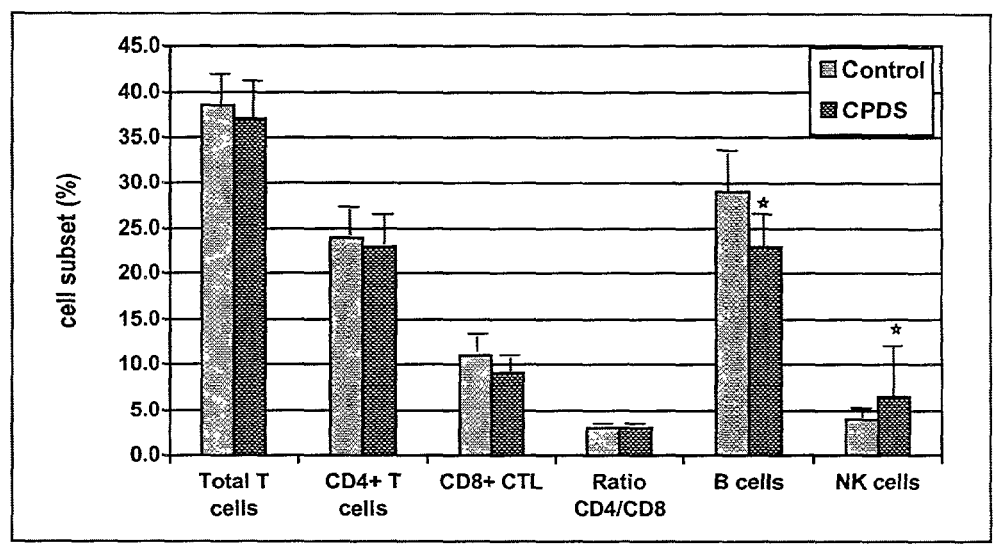
FIG. 4 depicts the composition of spleen cells in CPDS-treated Balb/c mice as a percentage of cells which are T cells, T helper cells, cytotoxic T cells, B cells, or NK cells. CD4 to CD8 ratio was calculated and shown in the figure. The measurements were taken after 30 days of CPDS treatment.

To count splenocytes, two chambers of the hemacytometer were counted and the mean was calculated. The total splenocyte count was calculated by the following formula: Total splenocyte count=mean count×10 (dilution factor)×$10^4$×suspension volume. The mean was calculated for each control and treated group. Student's T test was performed between the control group and the treated group. The p value was calculated for statistical significance. Following spleen homogenization, the total number of splenocytes isolated was counted using a standard trypan blue method which discriminates between viable and non viable cells. After 6 days and 30 days of treatment, the total splenocyte count was significantly reduced by 30.97% (p=0.04387) and 15.58% (0.04227) respectively (Table 6 and FIG. 1). This could be partially explained, at least for the 30 days treatment group, by the significant reduction of the B cells population (19.9%) as demonstrated by the immunophenotyping results (Table 6 and FIG. 4). No signs of necrosis or loss of splenocyte viability were observed.

Example 3

Immunomodulatory Effect of CPDS on Natural Killer (NK) Cells

NK cell activity was determined by using a standard NK assay (Coligan, J. E. et al. 1993. "In Vitro Assays for mouse lymphocyte function" Chapter 3, Current Protocol in Imnunology, John Wiley & Sons, New York) using YAC-1 cells (ATCC #TIB-160) as target cells. These cells were washed twice with HBSS, counted, and suspended at a concentration of $5×10^6$ cells/ml. About $5×10^6$ cells were labeled with 100 µCi of $^{51}Cr$. Cells were incubated 90 minutes at 37° C. in a 5% $CO_2$ humidified incubator and then washed three times with RPMI, counted, and suspended at a concentration of $1×10^5$ cells/ml in complete RPMI. About 100 µl of target cells (~$1×10^4$ cells) was put into each well of a round-bottom 96 wells plate.

Four dilutions of splenocytes were prepared: $2×10^7$ cells/ml, $1×10^7$ cells/ml, $0.5×10^7$ cells/ml, and $0.25×10^7$ cells/ml. A volume of 100 µl of each splenocyte dilution was plated in triplicate with the target cells for a final effector:target (E:T) ratio of 200:1, 100:1, 50:1 and 25:1.

A maximal control release was prepared in triplicate on each plate by adding 100 µl of 5% Triton X-100 solution instead of effector cells. Spontaneous release was prepared in triplicate on each plate by adding 100 µl of complete RPMI instead of effector cells. Plates were centrifuged and incubated 4 hours at 37° C. in a 5% $CO_2$ humidified incubator. After incubation, the supernatants were collected and the $^{51}Cr$ release was determined using a gamma counter. The average cpm count was calculated for each triplicate. The average cpm count for the total and spontaneous release was also calculated. The percentage (%) of specific lysis is calculated using the following formula:

$$\% \text{ of specific lysis} = \frac{(ER - SR)}{(TR - SR)} \times 100\%$$

Where, ER=Experimental release of $^{51}Cr$
TR=Total release of $^{51}Cr$
SR=Spontaneous release of $^{51}Cr$ The % of specific lysis for every ratio (200:1, 100:1, 50:1 and 25:1) was calculated. A graphic representation of the results is done: specific lysis % versus the ratio to verify the linearity. For BALB/c mice strains which usually show low NK activity, specific lysis corresponding to an E:T ratio of 200:1 is used to represent the data for each animal. The mean NK activity is then calculated for each control and treated group. Student's T test was performed between the control group and the treated group. The p value was calculated for statistical significance.

Figure 2:
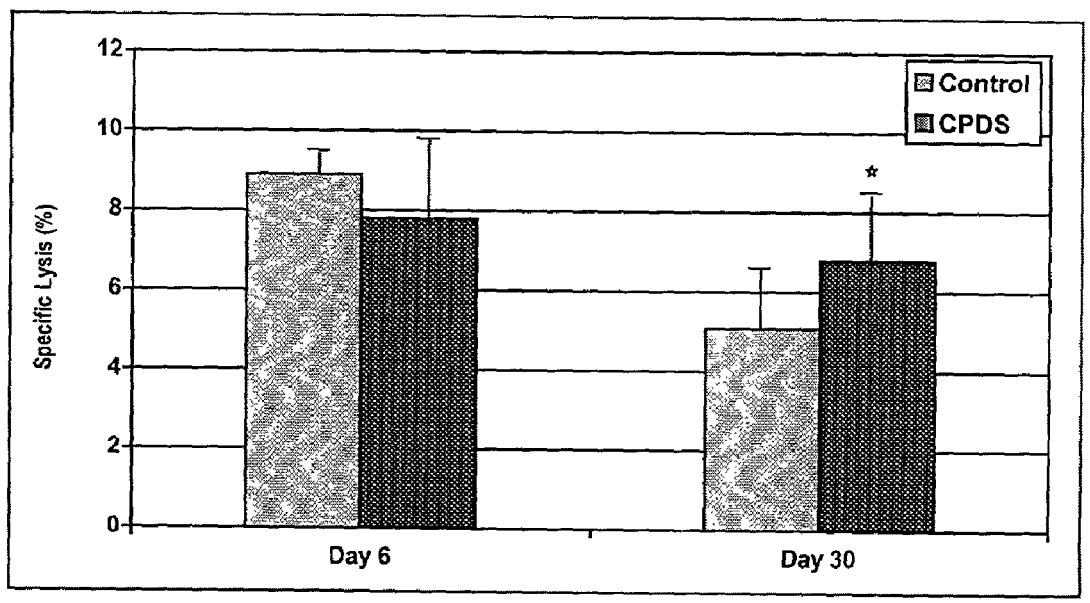
FIG. 2 depicts NK cell activity of Balb/c mice after 6 days and 30 days of treatment with CPDS.

In this assay, the effect on the NK activity of feeding Balb/c mice with compound CPDS for short term (6 days) and longer term (30 days) was evaluated. The NK cells are a lymphocyte subset with non specific cytotoxicity activity. Results are presented as the % of specific lysis of target cells for a ratio of 200:1 (Table 8 and FIG. 2). Balb/c mice normally show low NK activity which justifies the choice of the 200:1 ratio for the comparison between groups.

Figure 3:
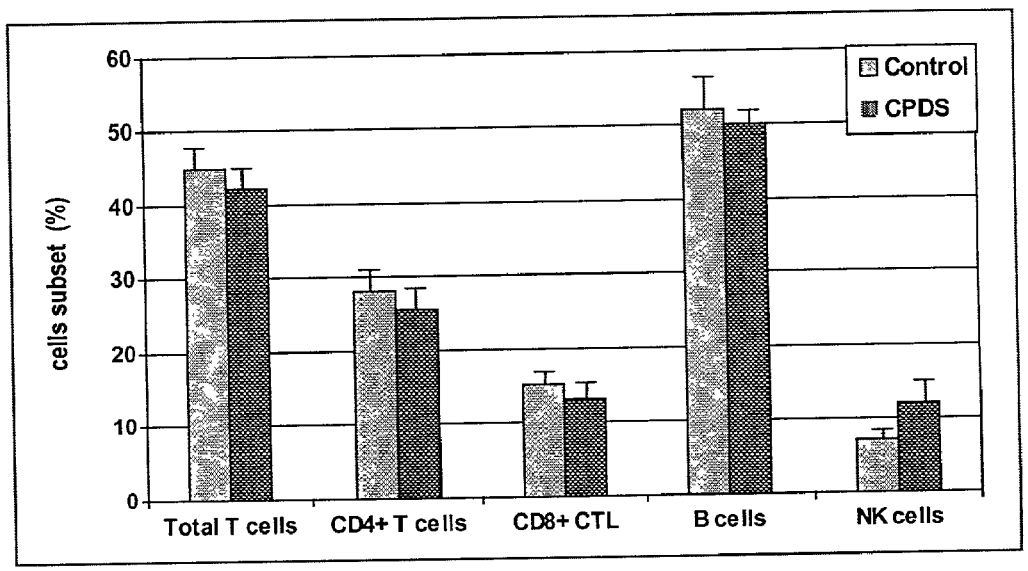
FIG. 3 depicts the composition of spleen cells in CPDS-treated Balb/c mice as a percentage of cells which are T cells, T helper cells, cytotoxic T cells, B cells, or NK cells. The measurements were taken after 6 days of CPDS treatment.

No significant effect were observed after 6 days of CPDS treatment (Table 6 and FIG. 3) but a significant increase (24.7%, p=0.01753) of the NK activity is observed after 30 days of treatment when compared to the control group. The increase of the NK activity was paralleled by an increase in their relative number, as shown in the immunophenotyping results (Table 9, FIG. 4).

The CPDS diet seems to activate NK cells. This potential to increase the number and the activity of the NK cells may present some therapeutic advantage against some viral infections.

Example 4

Immunophenotyping to Determine Effect of CPDS on Immune System

In general, the immunophenotyping technique consisted briefly of isolating cells from the peripheral blood or an organ (spleen or thymus), labeling them with a panel of antibodies specific for certain antigens of the membrane, and allowing to quantify the different populations. Analysis was performed by flow cytometry since antibodies were conjugated with a fluorochrome (Longbardi, Givan, A., 1994, Flow cytometry. First principles, Wiley-Liss Inc. New York.).

To immunophenotype immune cells, splenocytes were diluted to a concentration of $1 \times 10^6$ cells/ml. A total of $1 \times 10^6$ cells were distributed in a V-shape 96 well plate. A total of 7 wells were necessary for each sample. Plates were centrifuged 5 minutes at 1200 rpm. Supernatant was discarded and pellet were vortexed. Monoclonal antibodies were distributed in each wells according to the following set up:

| | |
|---|---|
| Well #1: | Control cells, no antibody |
| Well #2: | Isotypic control FITC-Conjugated (2 µl) |
| Well #3: | Isotypic control PF-Conjugated (5 µl) |
| Well #4: | $CD3^+$ FITC-Conjugated (2 µl) and $CD4^+PE$ Conjugated (5 µl) |
| Well #5 | $CD3^+$ FITC-Conjugated (2 µl) and $CT)8^+PE$ Conjugated (5 µl) |
| Well #6 | $CD3'$ FITC-Conjugated (2 µl) and $NK1.1^+PE$ Conjugated (5 µl) |
| Well #7 | $CD3^+$ FITC-Conjugated (2 µl) and $CD45B220^+PE$ Conjugated (5 µl) |

The antibodies used are commercially available from Becton Dickinson (San Jose, Calif.). The cells were incubated with the antibodies for 30 minutes on ice, washed three times with D-PBS+1% BSA, spun at 1200 rpm for 5 minutes using a multichannel pipette, suspended in 1 ml of paraformaldehyde 2% (v/v), and transferred into flow cytometry tubes. Samples were analyzed using EPICS XL from Beckman Coulter flow cytometer. Results were expressed as percentage of the population expressing the specific surface antigen. Live population of cells were gated upon using forward scatter (FS) vs. side scatter (SS) to distinguish live cells from dead cells. A total of 10,000 gated cells were counted for statistical relevance. The FL1 band pass filter (set at 525 nm) was used to detect fluoroscein isothiocyanate (FITC) fluorescence. The FL2 band pass filter (set at 575 nm) was used to detect phycoerythrin (PE) fluorescence. The cursors are set accordingly to delineate the positive region. This region should be relative to 1% of the unstained control (cell control). Results are expressed as % of positive population expressing the specific surface antigens. Student's T test was performed between the control group and the treated group. The p value was calculated for statistical significance.

Following 6 days of treatment with CPDS, no significant effect could be observed in the quantity of the different T and B cell populations. However, a tendency toward an increase of the NK population can be observed (Table 9, FIG. 3). After 30 days of treatment with CPDS, the spleen B cells population was significantly decreased by 19.9% (p=0.00106) when compared to the control group. CPDS diet also presented a statistically significant increase in NK cells numbers; this significant increase observed is 69.4% (p=0.03805) (Table 9, FIG. 4). This increase in quantity is paralleled by and increase in the NK cell activity. One tendency to decrease the number of $CD8^+T$ cells and increase the CD4/CD8 ratio is also observed after a 30 day-diet with CPDS.

Example 5

Use of CPDS for Mitogenic Proliferation

Splenocytes were diluted to a concentration of $1 \times 10^6$ cells/ml in complete RPMI media. Aliquots of 100 µl were transferred into a 96 well flat bottom plate. Mitogen stock solutions were prepared at a concentration of 1 mg/ml in D-PBS and frozen at −20° C. Working solution were prepared freshly in complete RPMI media at the following concentration (10×): 500 µg/ml PHA, 50 µg/ml concanavalin A (con A), and 50 µg/ml LPS. Aliquots of 100 µl of each mitogens were transferred in triplicate in the corresponding wells. Final concentration (1×) in each well was 50 µg/ml PHA, 5 µg/ml con A, and 5 µg/ml LPS. For negative control, 100 µl of complete RPMI media was added in triplicate, instead of the mitogens. Cells were incubated for a total of 72 hours in 37° C., 5% $CO_2$, humidified incubator. Twenty hours before the end of the incubation, 1 µCi per well of $^3H$-thymidine was added to each well. Cells were harvested using a Harvester® 96 from Tomtec. Filters were transferred into scintillation vials. Scintillation liquid, 4 ml was added to each vial. Radioactivity was counted using Beckman LS-6500 Beta counter. The results were expressed in CPM. The mean and standard deviation of triplicate samples are calculated. Results are expressed as stimulation index (SI) as follows:

$$SI = \frac{\text{experimental value} - \text{control value}}{\text{control value}} \times 100$$

where experimental value=with mitogens (PHA, ConA and LPS) and control value=with RPMI. For each mitogen, results were compared and Student's T test was performed between the control group and the treated group. The p value was calculated for statistical significance.

Figure 5:
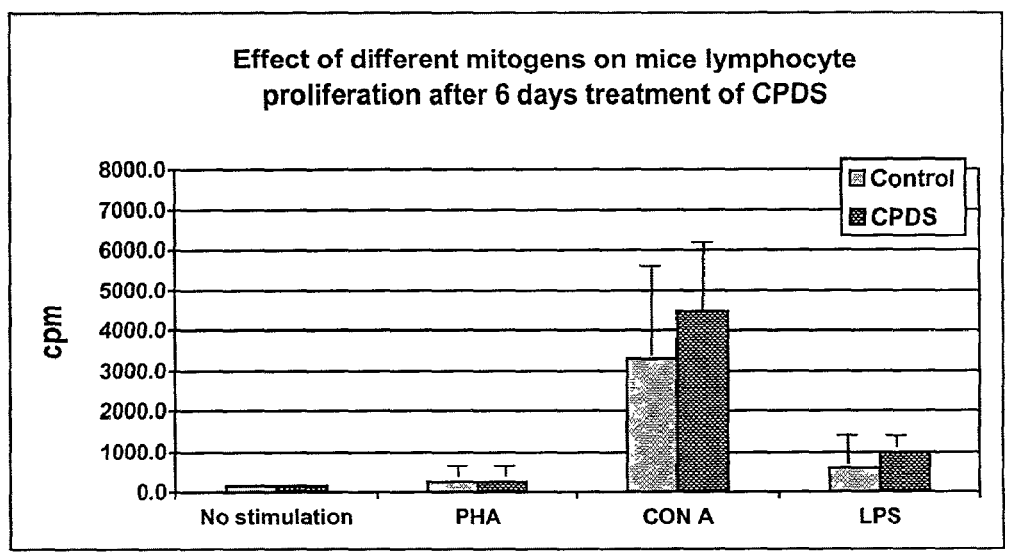
FIG. 5 depicts the effect of different mitogens on the proliferative ability of lymphocytes from male Balb/c mice either treated or untreated with CPDS for 6 days.
Figure 6:
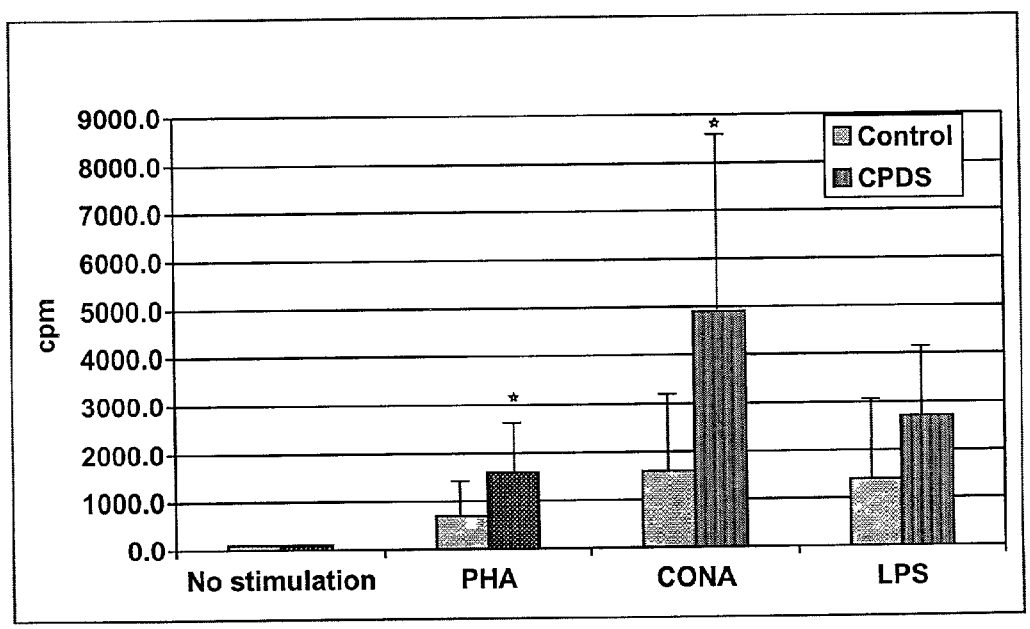
FIG. 6 depicts the effect of different mitogens on the proliferative ability of lymphocytes from male Balb/c mice either treated or untreated with CPDS for 30 days.

The lymphoproliferative response is a widely studied function of T and B lymphocytes. Three different mitogens with different specificity for different lymphocyte subsets were used. PHA and ConA are standard mitogens that stimulate mice T cells and LPS is a mitogen which stimulates B cells. Results are expressed in proliferation capacity (Table 10 and FIGS. 5 and 6). The in vivo/ex vivo results showed that after 6 days of treatment with CPDS, a tendency towards an increase in proliferation is observed with all three mitogens. After 30 days of treatment with CPDS, the lymphoproliferative response to PHA is significantly increased by 144.4% ($p=0.02280$). The proliferative response to ConA is also significantly increased by 210.2% ($p=0.01737$). However, a tendency to increase could be observed for the response to the B cell specific mitogen, LPS. These results showed that CPDS has the potential to stimulate the T cells mitogen-induced lymphoproliferative response. This potential may present some therapeutic application against some immune dysfunctions where the lymphoproliferative response is impaired (e.g., viral infections).

Example 6

Use of CPDS to Modulate Humoral Immunity

To perform KLH immunization, KLH was prepared in sterile D-PBS at a concentration of 150 μg in 0.1 ml. Animals were injected 0.1 ml of the preparation subcutaneously. After 15 days and just before sacrifice, a blood sample was collected from each mouse by cardiac puncture. Serum was obtained by centrifugation, aliquoted and frozen ($-20°$ C.) until used.

Immunodot blot assay was used to assess antibody production. Hybond-ECL membrane was used in the immunodot blot assay. A volume of 2 μl of different concentrations (0, 10, 50, 250 μg/ml) of KLH antigen was placed on the dry membrane. Antigen dots were allowed to dry overnight at $4°$ C. Membrane was blocked with a dry milk solution for 1 hour. Two μl of the antiserum diluted ½, ¼, ⅟16, ⅟32, ⅟64, ⅟128 and undiluted was put on the blot and incubated for 1 hour. The membrane was washed with TES buffer solution 3 times. Goat anti-mouse IgG antibodies coupled with horseradish peroxidase were put on the blot and incubated for 1 hour. The membrane was washed with TBS buffer solution 3 times. The antibody-antigen complexes were revealed by chemiluminescence: with ECL kit, following manufacturer's instructions. Revelation time was 1 minute. The membrane was exposed for 18 hours to film.

The lower serum dilution where an antibody response is apparent was chosen to calculate antibody titer. The antibody titer corresponded to the inverse of the dilution. The titer was converted to $\log_2$, e.g., $8=3$ ($\log_2$). Results were compared and Student's T test was performed between the control group and the treated group. The p value was calculated for statistical significance.

Figure 7:
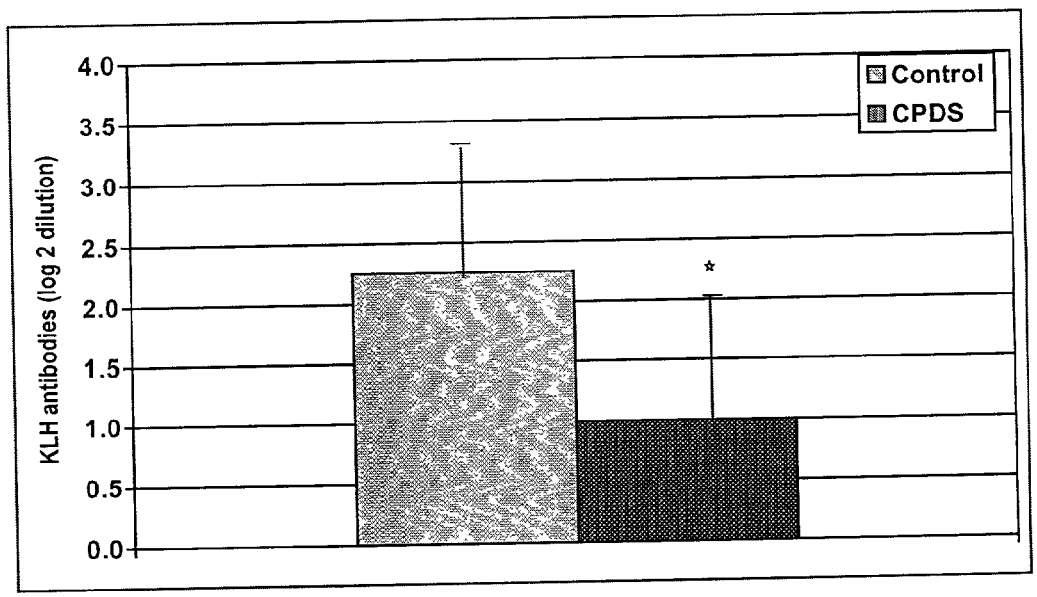
FIG. 7 depicts the level of antibody titer in response to keyhole limpet hemocyanine (KLH) in male Balb/c mice following treatment with CPDS for 45 days. Antibody titers were determined by dot blot and converted to $\log_2$ of the dilution.

For this experiment, animals were treated with CPDS for 30 days, immunized subcutaneously with keyhole limpet hemocyanin (KLH) and treated an additional 15 days, at which point blood was collected for antibody detection. Results demonstrate a significant decrease of 52.9% ($p=0.03654$) in primary antibody production in the CPDS treated group when compared to the control group (Table 11 and FIG. 7). The antibody titer to KLH was 1/4.29 (2.13 $\log_2$) for control group and 1/2.00 (1.00 $\log_2$) for CPDS-treated group. The decrease in the antibody production may be partially related to the significant decrease in the B cell population observed in the immunophenotyping results. However, no loss of reactivity was observed from the lymphoproliferative assay when B cells were stimulated with LPS. These results suggest that CPDS diet induces a suppressive effect on humoral function and that this suppressive effect may be due to the substantial loss observed in the number of antibody-producing B cells.

Example 7

Use of CPDS as Prophylatic Against Common Cold and Influenza

To use CPDS as a prophylaxis against the common cold and influenza, 140 mg to 280 mg of CPDS is ingested orally per day per person. The timing of the daily dosage is either morning, afternoon, or evening. The dosage is either taken at one time or multiple times, depending on the convenience for the individual taking the CPDS. The time course of taking CPDS is over several years.

Example 8

Use of CPDS in FIV-Infected Cats

A cat infected with feline immunodeficiency virus (FIV) was given 140 mg CPDS each morning. The CPDS was mixed with the cat's chow (food). The 140 mg CDPS dosage regimen was continued for 2 weeks. At this time, the cat's overall conditions (thin facial hair, dull eyes, excorations of the skin, appetite, general behavior) improved. After the 2 week timepoint, the dosage regimen was increased to 140 mg CPDS every morning and night (280 mg CPDS daily), mixed in the cat chow. After 30 days, the cat's overall conditions had improved. The cat's eyes were bright, facial hair was thick, appearance of hair was shiny, and the cat regained its appetite and gained 300 g in weight. The cat's general disposition was improved such that the cat exhibited active behavior of chasing and catching a bird, despite the fact the cat was lame in one of its front legs. The cat was given 280 mg CPDS daily for a total of 59 days and the cat showed improved physical condition, improved overall physical appearance, and improved behavior after the administration of CPDS.

After treatment for 100 days and a year and half after treatment, the cat appeared entirely healthy.

Example 9

Use of CPDS in FIV-Infected Cats for Immunomodulation

Two to four cats infected with FIV are monitored prior to the administration of CPDS to generate a baseline level of CD4 cell count and CD8 cell count. The cats are fed 140 mg to 280 mg CPDS in the cat chow on a daily basis. The cats are monitored on a regular interval to evaluate the efficacy of CPDS to immunodulate, e.g., change to the number of CD4 cells and/or CD8 cells. The CD4/CD8 ratio is also monitored for changes over the course of the CPDS treatment. Other parameters such as anti-FIV antibody titers and FIV titers are also measured to evaluate the efficacy of CPDS to immunodulate.

Example 10

Use of CPDS in FIV-Infected Cats for Immunomodulation

A very ill, young, spayed male cat ws presented with symptoms of feline immunodeficiency syndrome (FIDS). He had fever, diarrhea, and his glands were swollen. His coat was dull and the cat was listless.

His blood tested positive for feline immunodeficiency syndrome (FIV), as determined by ELISA testing with feline immunodeficiency virus antibody from Indexx Laboratories (Westbrook, Me.). The cat's weight upon presentation was 9.5 lbs.

Treatment of the cat with CPDS commenced the same day with a daily dose of 280 mg CPDS in the cat's diet. The regimen was continued for 30 days. The cat's health showed improvement after a few days. At the end of thirty days, the cat's fever had subsided, the diarrhea was gone, its glands were no longer swollen, but he still tested positive for the FIDS antibody. The hair on the cat's muzzle and back was still thin. CPDS treatment was continued at 140 mg/day for another 60 days. At this time, the cat appeared to be healed. His coat was rich and shiny, his eyes became bright, and his behavior was normal for a spayed male cat. The cat's weight after 60 days of treatment was 10.2 lbs, a gain of about 300 grams.

Example 11

Use of CPDS to Treat Cold Sores

CPDS is used to treat cold sores, either related or unrelated to herpes virus. A pomade is made by combining CPDS with a glycerin-based lip ointment or cream in the ratio of 2 parts CPDS (by weight) to 98 parts cream (by weight). The pomade is applied topically to the cold sore(s) on a daily basis until the area in which cold sore(s) is located heals.

Example 12

Immunomodulatory Effects of CPDS on Neutrophils

CPDS is administered to individual at a dosage of 140 mg to 280 mg (non-toxic amount) on a daily basis. The immunomodulatory effect of the CPDS on neutrophil activity is monitored by determining the rate of phagocytosis by the neutrophils, the amount of material phagocytosed, and measuring oxidative burst. In addition, the staining and morphology of the neutrophil can be monitored.

Example 13

Immunomodulatory Effects of CPDS on Macrophages

CPDS is administered to individual at a dosage of 140 mg to 900 mg (non-toxic amount) on a daily basis. The immunomodulatory effect of the CPDS on macrophage activity is monitored by determining the rate of phagocytosis by the macrophages, the amount of material phagocytosed, and measuring oxidative burst. In addition, the staining and morphology of the macrophage can be monitored.

TABLE 3

Animal Groups

| Animal group | No. of animals | Diet used | Days on Diet | Immune testing |
|---|---|---|---|---|
| Group 1 | 8 | Standard Purina mouse chow | 30 days | Cellular immunity |
| Group 2 | 8 | CPDS diet | 30 days | Cellular immunity |
| Group 3 | 8 | Standard Purina mouse chow | 45 days | Humoral immunity |
| Group 4 | 8 | CPDS diet | 45 days | Humoral immunity |
| Group 5 | 3 | Standard Purina mouse chow | 6 days | Cellular immunity |
| Group 6 | 3 | CPDS diet | 6 days | Cellular immunity |

TABLE 4

Total CPDS Diet Consumed by Animals

| Animal Groups | Mouse chow + CPDS Ingested (g) | Total CPDS ingested (g) | Total CPDS ingested/ mouse (g) |
|---|---|---|---|
| Group 2 (30 days CPDS diet) | | | |
| 2-1 | 264.60 | 1.06 | 0.53 |
| 2-2 | 225.90 | 0.90 | 0.45 |
| 2-3 | | | |
| 2-4 | 237.60 | 0.95 | 0.49 |
| 2-5 | | | |
| 2-6 | 229.00 | 0.92 | 0.46 |
| 2-7 | | | |
| 2-8 | | | |
| Mean + S.D. | 239.28 + 17.5 | 0.96 ± 0.07 | 0.48 ± 0.04 |
| Group 4 (45 days CPDS diet) | | | |
| 4-1 | 292.30 | 1.17 | 0.59 |
| 4-2 | | | |
| 4-3 | 231.90 | 0.93 | 0.47 |
| 4-4 | | | |
| 4-5 | 285.80 | 1.14 | 0.57 |
| 4-6 | | | |
| 4-7 | 239.00 | 0.96 | 0.48 |
| 4-8 | | | |
| Mean ± S.D. | 262.25 ± 31.1 | 1.05 ± 0.12 | 0.53 ± 0.06 |
| Group 6 (6 days diet) | | | |
| 6-1 | 78.40 | 0.31 | 0.10 |
| 6-2 | | | |
| 6-3 | | | |

TABLE 5

| Animal Groups | Day 0 | Day 6 | Day 14 | Day 21 | Day 21 | Day 35 | Day 45 |
|---|---|---|---|---|---|---|---|
| GROUP 1 (30 days normal diet) | | | | | | | |
| 1-836 | 15.88 | 19.63 | 21.26 | 23.51 | 24.38 | | |
| 2-835 | 13.51 | 17.87 | 19.74 | 21.30 | 22.65 | | |
| 3-834 | 14.48 | 18.78 | 20.48 | 21.34 | 23.59 | | |
| 4-833 | 13.01 | 17.98 | 20.47 | 20.81 | 22.59 | | |
| 5-830 | 15.17 | 18.40 | 20.66 | 21.33 | 23.05 | | |
| 6-829 | 14.31 | 17.94 | 19.02 | 20.56 | 22.21 | | |
| 7-867 | 13.58 | 17.39 | 17.36 | 19.12 | 21.01 | | |
| 8-822 | 13.72 | 17.12 | 18.52 | 19.70 | 21.50 | | |
| Mean ± S.D. | 14.21 ± 0.95 | 18.14 ± 0.8 | 19.69 ± 1.3 | 20.96 ± 1.0 | | | |
| GROUP 2 (30 days CPDS diet) | | | | | | | |
| 1-838 | 15.87 | 18.64 | 19.66 | 20.10 | 21.96 | | |
| 2-837 | 15.18 | 19.84 | 20.46 | 21.36 | 22.76 | | |
| 3-832 | 12.76 | 15.20 | 17.47 | 18.72 | 19.99 | | |
| 4-831 | 15.67 | 18.31 | 19.96 | 21.20 | 22.98 | | |
| 5-857 | 15.69 | 18.66 | 19.78 | 21.36 | 22.80 | | |
| 6-858 | 15.29 | 18.54 | 19.09 | 20.58 | 22.31 | | |
| 7-859 | 15.25 | 17.98 | 19.84 | 20.79 | 22.57 | | |
| 8-861 | 13.28 | 16.92 | 18.65 | 19.87 | 20.94 | | |
| Mean ± S.D. | 14.87 ± 1.18 | 17.89 + 1.2 | 19.36 ± 0.9 | 20.50 ± 0.9 | 22.04 ± 1.0 | | |
| p value vs. group 1 | 0.11701 | 0.13815 | 0.28832 | 0.21310 | 0.14656 | | |
| GROUP 3 (45 days normal diet) | | | | | | | |
| 1-855 | 14.00 | 15.40 | 17.58 | 18.87 | 21.12 | 21.48 | 22.60 |
| 2-856 | 16.00 | 19.76 | 20.02 | 21.09 | 22.80 | 22.73 | 24.42 |
| 3-860 | 14.56 | 17.69 | 18.91 | 19.93 | 21.63 | 22.33 | 23.77 |
| 4-862 | 14.54 | 18.24 | 20.45 | 20.84 | 23.44 | 24.37 | 26.03 |
| 5-864 | 15.31 | 18.84 | 20.52 | 21.36 | 22.59 | 23.31 | 24.19 |
| 6-863 | 16.57 | 19.87 | 21.19 | 22.50 | 24.18 | 25.07 | 26.33 |
| 7-815 | 13.59 | 15.22 | 17.51 | 18.54 | 20.53 | 21.53 | 22.37 |
| 8-814 | 14.63 | 19.30 | 20.62 | 21.93 | 23.82 | 24.40 | 25.69 |
| Mean ± S.D. | 14.904 ± 1.0 | 18.04 ± 1.8 | 19.60 ± 1.4 | 20.63 ± 1.4 | 22.51 ± 1.3 | 23.15 ± 1.3 | 24.43 ± 1.5 |
| GROUP 4 (45 days CPDS diet) | | | | | | | |
| 1-866 | 13.58 | 17.25 | 18.57 | 19.72 | 21.40 | 21.82 | 22.71 |
| 2-865 | 16.07 | 18.57 | 20.58 | 21.59 | 23.72 | 24.00 | 24.66 |
| 3-812 | 14.28 | 17.03 | 18.25 | 19.22 | 20.35 | 20.91 | 20.96 |
| 4-813 | 13.75 | 16.46 | 17.66 | 18.38 | 20.18 | 20.95 | 21.78 |
| 5-818 | 14.89 | 17.79 | 18.83 | 19.40 | 21.41 | 22.47 | 23.15 |
| 6-820 | 15.10 | 18.38 | 18.57 | 19.35 | 21.14 | 21.39 | 22.10 |
| 7-816 | 13.67 | 16.98 | 18.02 | 19.45 | 21.40 | 22.28 | 23.09 |
| 8-817 | 15.20 | 19.46 | 20.86 | 21.74 | 23.19 | 23.68 | 23.80 |
| Mean ± S.D. | 14.57 ± 0.8 | 17.74 ± 1.0 | 18.92 ± 1.1 | 19.86 ± 1.1 | 21.60 ± 1.2 | 22.19 ± 1.1 | 22.78 ± 1.1 |
| p value vs. Group 3 | 0.24730 | 0.34559 | 0.15672 | 0.12369 | 0.08772 | 0.07534 | 0.01432 |
| GROUP 5 (6 days normal diet) | | | | | | | |
| 1-841 | 14.90 | 18.13 | | | | | |
| 2-839 | 16.22 | 18.60 | | | | | |
| 3-828 | 14.67 | 17.79 | | | | | |
| Mean | 15.26 ± 0.8 | 18.17 ± 0.4 | | | | | |
| GROUP 6 (6 days CPDS diet) | | | | | | | |
| 1-844 | 13.90 | 17.60 | | | | | |
| 2-843 | 16.04 | 19.18 | | | | | |
| 3-842 | 15.50 | 18.43 | | | | | |
| Mean ± S.D. | 15.15 ± 1.1 | 18.40 ± 0.7 | | | | | |
| p value vs. Group 5 | 0.44581 | 0.33861 | | | | | |

TABLE 6

Effect of CPDS diet on different parameters of the immune system in adult BALB/c mice

| | | 6 days (No of animals = 3) | 30 days (No of animals = 8) |
|---|---|---|---|
| Total splenocyte count | | ⇩ 30.9% p = 0.04387 | ⇩ 15.6% p = 0.04227 |
| NK activity | | No effect | ⇧ 24.7% p = 0.01753 |
| Immunophenotyping | Total T cells | No effect | No effect |
| | T CD4+ | No effect | No effect |
| | T CD8+ | No effect | ⇩ tendency |
| | Ratio CD4/CD8 | No effect | ⇧ tendency |
| | B cells | No effect | ⇩ 19.9% p = 0.00106 |
| | NK cells | ⇧ tendency | ⇧ 69.4% p = 0.03050 |
| Mitogenic Proliferation (SI) | PHA | No effect | ⇧ 142.6% (SI) p = 0.02330 |
| | CON A | ⇧ tendency | ⇧ 207.0% (SI) p = 0.01997 |
| | LPS | No effect | ⇧ tendency |
| Humoral Immunity | Antibody production (45 days) | | ⇩ 52.9% p = 0.03654 |

TABLE 7

Total Lymphocyte Counts

| Animal Group | Sample # | Total Lymphocyte Counts |
|---|---|---|
| Group 5 (6 days on normal diet) | 5-1 | 5.18 × 10$^7$ |
| | 5-2 | 5.65 × 10$^7$ |
| | 5-3 | 7.25 × 10$^7$ |
| | Mean | 6.03 × 10$^7$ |
| Group 6 (6 days on CPDS diet) | 6-1 | 4.82 × 10 |
| | 6-2 | 3.08 × 10$^7$ |
| | 6-3 | 4.58 × 10$^7$ |
| | Mean | 4.16 × 10$^7$ |
| | Variation | −30.97% |
| | p value vs. group 51 | 0.04387 |
| Group 1 (30 days on normal diet) | G1-1 | 7.30 × 10$^7$ |
| | G1-2 | 3.87 × 10$^7$ |
| | G1-3 | 6.08 × 10$^7$ |
| | G1-4 | 6.66 × 10$^7$ |
| | G1-5 | 6.63 × 10$^7$ |
| | G1-6 | 6.27 × 10$^7$ |
| | G1-7 | 6.26 × 10$^7$ |
| | G1-8 | 4.42 × 10$^7$ |
| | Mean | 5.94 × 10$^7$ |
| Group 2 (30 days on CPDS diet) | G2-1 | 3.94 × 10$^7$ |
| | G2-2 | 5.18 × 10$^7$ |
| | G2-3 | 6.03 × 10$^7$ |
| | G2-4 | 4.47 × 10$^7$ |
| | G2-5 | 5.54 × 10$^7$ |
| | G2-6 | 5.91 × 10$^7$ |
| | G2-7 | 4.77 × 10$^7$ |
| | G2-8 | 4.25 × 10$^7$ |
| | Mean | 5.01 × 10$^7$ |
| | variation | −15.58% |
| | p value vs. group 1 | 0.04227 |

TABLE 8

NK cell Activity

| Animal Groups | Sample # | NK activity (%) |
|---|---|---|
| Group 5 (6 days on normal diet) | 5-1 | 9.6 |
| | 5-2 | 8.4 |
| | 5-3 | 9.4 |
| | Mean ± S.D. | 9.1 ± 0.6 |
| Group 6 (6 days on CPDS diet) | 6-1 | 6.6 |
| | 6-2 | 10.2 |
| | 6-3 | 7.0 |
| | Mean ± S.D. | 7.9 ± 2.0 |
| | Variation | −13.1% |
| | p value vs. group 5 | 0.18662 |
| Group 1 (30 days on normal diet) | G1-1 | 5.3 |
| | G1-2 | 4.9 |
| | G1-3 | 6.6 |
| | G1-4 | 5.2 |
| | G1-5 | 5.4 |
| | G1-6 | 5.6 |
| | G1-7 | 6.5 |
| | G1-8 | 3.9 |
| | Mean ± S.D. | 5.4 ± 0.9 |
| Group 2 (30 days on CPDS diet) | G2-1 | 8.7 |
| | G2-2 | 7.9 |
| | G2-3 | 5.0 |
| | G2-4 | 6.9 |
| | G2-5 | 6.3 |
| | G2-6 | 5.6 |
| | G2-7 | 5.6 |
| | G2-8 | 8.2 |
| | Mean ± S.D. | 6.8 ± 1.4 |
| | variation | 24.7% |
| | p value vs. Group 1 | 0.01753 |

TABLE 9

Immunophenotyping

| Animal Groups | Sample # | Total T cells (%) | CD4+ (%) | CD8+ (%) | Ratio CD4/CD8 | B cells (%) | NK cells (%) |
|---|---|---|---|---|---|---|---|
| Group 5 (6 days on normal diet) | 5-1 | 41.4 | 25.4 | 13.6 | 1.87 | 55.7 | 6.1 |
| | 5-2 | 47.3 | 29.7 | 15.1 | 1.97 | 48.9 | 7.4 |
| | 5-3 | 46.4 | 29.6 | 15.1 | 1.96 | 47.8 | 9.4 |
| | Mean ± S.D. | 45.0 ± 3.2 | 28.2 ± 2.5 | 14.6 ± 0.9 | 1.93 ± 0.06 | 50.8 ± 4.3 | 7.6 ± 1.7 |
| Group 6 (6 days on CPDS diet) | 6-1 | 42.8 | 26.4 | 14.0 | 1.89 | 49.8 | 9.7 |
| | 6-2 | 38.6 | 23.3 | 12.6 | 1.85 | 50.7 | 14.1 |
| | 6-3 | 42.9 | 27.8 | 14.2 | 1.96 | 50.3 | 9.1 |
| | Mean ± S.D. | 41.4 ± 2.5 | 25.8 ± 2.3 | 13.6 ± 0.9 | 1.90 ± 0.06 | 50.3 ± 0.5 | 11.9 ± 2.7 |
| | variation (%) | −8.0 | −8.5 | −6.8 | −1.8 | −1.0 | 43.5 |
| | p value vs. Group 5 | 0.09772 | 0.14218 | 0.11574 | 0.24662 | 0.42025 | 0.07293 |
| Group 1 | G1-1 | 39.0 | 24.6 | 11.0 | 2.24 | 32.4 | 6.0 |

TABLE 9-continued

Immunophenotyping

| Animal Groups | Sample # | Total T cells (%) | CD4+ (%) | CD8+ (%) | Ratio CD4/CD8 | B cells (%) | NK cells (%) |
|---|---|---|---|---|---|---|---|
| (30 days on normal diet) | G1-2 | 42.1 | 27.5 | 12.7 | 2.17 | 33.3 | 3.8 |
| | G1-3 | 34.0 | 21.9 | 8.9 | 2.46 | 34.2 | 5.6 |
| | G1-4 | 42.0 | 26.2 | 13.5 | 1.94 | 29.0 | 3.2 |
| | G1-5 | 38.7 | 23.5 | 9.7 | 2.43 | 26.4 | 3.1 |
| | G1-6 | 39.1 | 25.2 | 10.2 | 2.47 | 28.9 | 3.6 |
| | G1-7 | 36.1 | 22.4 | 9.5 | 2.37 | 27.4 | 3.8 |
| | G1-8 | 40.3 | 25.3 | 10.4 | 2.43 | 22.5 | 3.4 |
| | Mean ± S.D. | 38.9 ± 2.8 | 24.6 ± 1.9 | 10.7 ± 1.6 | 2.31 ± 0.19 | 29.3 + 3.9 | 4.1 ± 1.1 |
| Group 2 (30 days on CPDS diet) | G2-1 | 35.8 | 21.7 | 8.5 | 2.55 | 24.0 | 16.8 |
| | G2-2 | 36.8 | 21.7 | 9.58 | 2.27 | 25.9 | 4.8 |
| | G2-3 | 39.6 | 24.0 | 10.2 | 2.35 | 25.0 | 11.9 |
| | G2-4 | 44.6 | 28.3 | 11.5 | 2.46 | 21.5 | 3.72 |
| | G2-5 | 39.8 | 25.7 | 9.66 | 2.66 | 23.8 | 4.8 |
| | G2-6 | 37.5 | 23.2 | 7.92 | 2.93 | 22.3 | 2.6 |
| | G2-7 | 36.0 | 22.2 | 8.54 | 2.60 | 24.8 | 5.56 |
| | G2-8 | 37.4 | 22.1 | 10.5 | 2.1 | 20.1 | 4.76 |
| | Mean ± S.D. | 38.4 ± 2.9 | 23.6 ± 2.3 | 9.6 ± 1.2 | 2.49 ± 0.26 | 23.4 ± 2.0 | 6.9 ± 4.9 |
| | variation (%) | −1.2 | −3.9 | −11.0 | 7.7 | −19.9 | 69.4 |
| | p value vs. group 1 | 0.37123 | 0.19050 | 0.05834 | 0.06661 | 0.00106 | 0.03805 |

TABLE 10

Mitogenic Proliferation

| Animal Groups | No stimulation | PHA | CON A | LPS |
|---|---|---|---|---|
| Group 5 (6 days on normal diet) | | | | |
| 5-1 | 24.0 | 124.0 | 1367.3 | 386.7 |
| 5-2 | 85.3 | 133.3 | 2825.3 | 323.3 |
| 5-3 | 129.0 | 318.0 | 5922.0 | 1324.0 |
| Mean ± S.D. | 79.4 ± 52 | 191.8 ± 109 | 3371.5 ± 2326 | 678.0 ± 560 |
| Group 6 (6 days on CPDS diet) | | | | |
| 6-1 | 78.0 | 237.3 | 4876.7 | 1052.0 |
| 6-2 | 34.7 | 120.0 | 2532.0 | 670.0 |
| 6-3 | 38.7 | 258.7 | 5916.7 | 1091.3 |
| Mean ± S.D. | 50.5 ± 23 | 205.3 ± 74 | 4441.8 ± 1733 | 937.9 ± 232 |
| p value vs. Group 5 | 0.21761 | 0.43391 | 0.27879 | 5.24977 |
| Group 1 (30 days on normal diet) | | | | |
| G1-1 | 81.3 | 639.3 | 2011.3 | 1558.7 |
| G1-2 | 70.0 | 1938.7 | 3928.7 | 4183.3 |
| G1-3 | 66.0 | 68.7 | 82.7 | 94.0 |
| G1-4 | 68.7 | 1093.3 | 3232.7 | 2770.0 |
| G1-5 | 84.7 | 74.7 | 82.7 | 96.7 |
| G1-6 | 62.7 | 81.3 | 116.0 | 95.3 |
| G1-7 | 58.0 | 1369.3 | 3040.0 | 2676.0 |
| G1-8 | 64.0 | 81.3 | 100.7 | 75.3 |
| Mean ± S.D. | 69.4 ± 9 | 668.3 ± 725 | 1574.3 ± 1663 | 1443.7 ± 1609 |
| Group 1 (30 days on CPDS diet) | | | | |
| G2-1 | 78.0 | 3565.3 | 6928.7 | 3799.3 |
| G2-2 | 69.3 | 1168.0 | 2621.3 | 1426.0 |
| G2-3 | 66.7 | 2175.3 | 11240.7 | 4760.0 |
| G2-4 | 82.0 | 2300.0 | 8041.3 | 4304.7 |
| G2-5 | 57.3 | 603.3 | 915.3 | 842.0 |
| G2-6 | 72.7 | 717.3 | 1023.3 | 1407.3 |
| G2-7 | 72.0 | 1652.6 | 3308.7 | 2438.0 |
| G2-8 | 58.7 | 886.0 | 4993.3 | 2039.3 |
| Mean ± S.D. | 69.6 ± 8 | 1633.4 ± 1010 | 4984.1 ± 3641 | 2627.1 ± 1475 |
| Variation(%) | 0.2 | 144.4 | 210.2 | 82.0 |
| p value | 0.48534 | 0.02280 | 0.01737 | 0.07374 |

TABLE 11

| Animal | Sample # | Serum dilution | dilution log 2 |
|---|---|---|---|
| Group 3 (45 days on normal diet) | G3-1 | 1/8 | 3 |
| | G3-2 | 1/8 | 3 |
| | G3-3 | 1/4 | 2 |
| | G3-4 | 1/4 | 2 |
| | G3-5 | 1/16 | 4 |
| | G3-6 | 1/4 | 2 |
| | G3-7 | 1/2 | 1 |
| | G3-8 | 0 | 0 |
| | Mean ± S.D. | | 2.13 ± 1.25 |
| | Ab. Titer | | 1/4.29 |
| Group 4 (45 days on CPDS diet) | G4-1 | 1/4 | 2 |
| | G4-2 | 0 | 0 |
| | G4-3 | 1/4 | 2 |
| | G4-4 | 0 | 0 |
| | G4-5 | 1/4 | 2 |
| | G4-6 | 0 | 0 |
| | G4-7 | 0 | 0 |
| | G4-8 | 1/4 | 2 |
| | Mean ± S.D. | | 1.00 ± 1.07 |
| | variation (%) | | −52.94 |
| | p value vs. Group 3 | | 0.03654 |
| | Ab. Titer | | 1/2.00 |

Humoral Response to KLH immunization

What is claimed is:

1. A method for modulating an immune response comprising:
    identifying an individual suffering from an ailment selected from the group consisting of: renal failure in systemic lupus erythmatosus, bacterial endocarditis, mycosis and fungal infection; and
    administering to the individual an effective amount of a thione-forming disulfide having the general formula R-S-S-R, wherein the R group comprises an unsubstituted or substituted pyridinyl group thereby modulating the immune response and treating the ailment;
    wherein the thione-forming disulfide is selected from the group consisting of: 6,6'-dithiodinicotinic acid (CPDS), 6,6'-dithiodinicotinic acid diethyl ester, and 2,2'-dithiobis-isonicotinic acid.

2. The method according to claim 1 wherein the immune response is a cellular immune response.

3. The method according to claim 2 wherein the cellular immune response is a T cell response and wherein cell populations are increased or lymphoproliferative activity is increased.

4. The method according to claim 1 wherein the immune response is an innate immune response.

5. The method according to claim 4 wherein the innate immune response comprises increasing the natural killer cell population and NK activity.

6. The method according to claim 1 wherein the immune response is a humoral immune response.

7. The method according to claim 6 wherein the humoral immune response is a decrease in B cell population or B cell response.

8. The method according to claim 7 wherein the humoral immune response is an increase or decrease in antibody secretion.

9. The method according to claim 1 wherein the immune response is biased towards a Th1-type response.

10. The method according to claim 9 wherein the Th1-type response is an increased cell population of NK cells or T cells.

11. The method according to claim 9 wherein the Th1-type response is an increased activity in NK cells or T cells.

12. The method according to claim 1 wherein the immune response is an increase in cytokine levels.

13. The method according to claim 12 wherein the cytokine is selected from the group consisting of IL-2, IFN-.gamma., IFN-.alpha., IFN-.beta., IL-12, TNF-.alpha., and TNF-.beta.

14. The method according to claim 1 wherein the immune response is an increase in chemokine levels.

15. The method according to claim 14 wherein the chemokine is selected from the group consisting of RANTES, IL-8, MIP-1.alpha., MIP-1.beta., MCP-1, lymphotactin, and eotaxin.

16. The method according to claim 1, wherein the thione-forming disulfides are administered in a pharmaceutically acceptable carrier.

* * * * *